United States Patent
Logan et al.

(10) Patent No.: US 10,214,786 B2
(45) Date of Patent: Feb. 26, 2019

(54) WASTEWATER TREATMENT FOR THE PRODUCTION OF MICROBIAL BIOMASS

(71) Applicant: PROCELL INVESTMENTS LIMITED, Tortola (VG)

(72) Inventors: Andrew J. Logan, Glendale, CO (US); Kathryn R. Spangler, Glendale, CO (US)

(73) Assignee: PROCELL INVESTMENTS LIMITED, Tortola (VG)

( * ) Notice: Subject to any disclaimer, the term of this patent is extended or adjusted under 35 U.S.C. 154(b) by 0 days.

(21) Appl. No.: 14/894,777

(22) PCT Filed: Oct. 4, 2013

(86) PCT No.: PCT/US2013/063433
§ 371 (c)(1),
(2) Date: Nov. 30, 2015

(87) PCT Pub. No.: WO2014/193466
PCT Pub. Date: Dec. 4, 2014

(65) Prior Publication Data
US 2016/0108480 A1    Apr. 21, 2016

Related U.S. Application Data

(60) Provisional application No. 61/828,504, filed on May 29, 2013.

(51) Int. Cl.
| | |
|---|---|
| *C12Q 3/00* | (2006.01) |
| *C02F 3/12* | (2006.01) |
| *A23K 10/12* | (2016.01) |
| *A23K 10/38* | (2016.01) |

(52) U.S. Cl.
CPC ............... *C12Q 3/00* (2013.01); *A23K 10/12* (2016.05); *A23K 10/38* (2016.05); *C02F 3/12* (2013.01); *C02F 2209/08* (2013.01); *Y02P 60/873* (2015.11); *Y02W 10/15* (2015.05)

(58) Field of Classification Search
CPC ..... Y02W 10/15; Y02W 10/37; Y02W 10/12; C02F 2301/106; C02F 1/32; C02F 3/226; C02F 1/24; C02F 2101/20; C02F 11/185; C02F 3/02; C02F 3/1268; C02F 3/301; C02F 2003/001; C02F 2101/105; C02F 3/12; C02F 2209/08; A23K 10/12; A23K 10/38; A23K 1/007; A23K 1/06; C12Q 3/00; Y02P 60/873
See application file for complete search history.

(56) References Cited

U.S. PATENT DOCUMENTS

| | | | | |
|---|---|---|---|---|
| 5,225,340 A | * | 7/1993 | Nghiem | C02F 1/681 435/168 |
| 5,851,398 A | * | 12/1998 | Adey | C02F 3/32 210/602 |
| 6,096,215 A | * | 8/2000 | Fang | C02F 3/00 210/610 |
| 6,689,274 B1 | * | 2/2004 | Northrop | C02F 3/00 210/170.08 |
| 2003/0232107 A1 | * | 12/2003 | Terry | A23K 40/10 426/2 |
| 2006/0000768 A1 | * | 1/2006 | Miklos | C02F 3/006 210/605 |
| 2008/0203015 A1 | * | 8/2008 | Marston | C02F 3/12 210/610 |
| 2008/0210610 A1 | * | 9/2008 | Whiteman | C02F 3/12 210/143 |
| 2010/0213122 A1 | * | 8/2010 | Tatarko | C02F 3/2806 210/605 |
| 2011/0073543 A1 | * | 3/2011 | Shafer | C02F 3/006 210/610 |
| 2012/0088278 A1 | * | 4/2012 | Kim | C12M 21/02 435/101 |
| 2013/0040351 A1 | * | 2/2013 | Liu | C02F 3/1221 435/136 |

FOREIGN PATENT DOCUMENTS

| | | | |
|---|---|---|---|
| WO | WO 2008/100999 A1 | * | 8/2008 |
| WO | WO2009059163 A1 | * | 5/2009 |
| WO | WO 2009147693 A2 | * | 12/2009 ................ C02F 9/00 |

OTHER PUBLICATIONS

Search Report of PCT/US13/63433, dated Mar. 26, 2014.*
Jefferson, B. et al. Nutrient Addition to Enhance Biological Treatment of Greywater. 2001. Water Res. vol. 35, No. 11, pp. 27-2-27-10: entire document.*

* cited by examiner

*Primary Examiner* — Debbie K Ware
(74) *Attorney, Agent, or Firm* — CBM Patent Consulting, LLC

(57) ABSTRACT

A method of producing microbial biomass include providing a wastewater stream and determining the concentration of micronutrients selected from the group consisting of aluminum, boron, cobalt, magnesium, manganese, and zinc, and any combination thereof, in the wastewater stream. The method also includes determining the biological oxygen demand (BOD) normalized dose of the micronutrients, and modulating the concentration of at least one micronutrient in the wastewater stream to provide a micronutrient-modulated wastewater stream. The method further includes growing microbial biomass in the micronutrient-modulated wastewater stream.

20 Claims, 2 Drawing Sheets

WASTEWATER TREATMENT FOR THE PRODUCTION OF MICROBIAL BIOMASS

PRIORITY TO RELATED APPLICATION

This application is a U.S. national stage application of International Application No. PCT/US2013/063433, filed on Oct. 4, 2013, and claims priority to U.S. Provisional Application No. 61/828,504 filed May 29, 2013, titled "WASTEWATER TREATMENT FOR THE PRODUCTION OF MICROBIAL BIOMASS", the entire disclosures of which are incorporated herein by reference in their entirety.

FIELD OF THE DISCLOSURE

The disclosure provided herein generally relates to the field of wastewater treatment and, more particularly, to methodologies for the treatment of wastewater to produce microbial biomass. The methods provided herein are useful in that they enhance wastewater treatment and yield protein-rich microbial biomass, useful, inter alia, in the preparation of animal feed.

BACKGROUND

The manufacture of many industrially made products involves the use of water, resulting in the generation of an aqueous waste stream as a by-product of the manufacturing process. In order to limit environmental challenges associated with disposal of waste streams, organic pollutants are often removed from waste streams by aerobic biological water treatment i.e. by cultivating microbial organisms to convert the pollutants present in aqueous waste streams to produce microbial cell mass, carbon dioxide and other metabolites, and water that is relatively free of contaminants.

A typical biological wastewater treatment process involves the cultivation of microbial cells within an aerated reactor comprising the aqueous wastewater and microbial cells grown in suspension in the aqueous wastewater. The microbial cells produced in the aeration reactor are normally allowed to overflow continuously into a solid-liquid separator (e.g. a gravity clarifier, dissolved air flotation vessel, or membrane-based system) generating a clear effluent and microbial biomass, frequently referred to as "activated sludge". The effluent is then discharged in a local waterway, injected underground or discharged in any other appropriate manner, and the microbial mass, is in part returned to the aeration reactor (frequently referred to as "return activated sludge" or "RAS"), and in part disposed as solid waste (frequently referred to as "waste activated sludge" or "WAS").

Known wastewater treatment processes exhibit several drawbacks. First, the waste activated sludge component must be disposed and the disposal costs are frequently a significant cost component in the operation of a wastewater plant. However, waste activated sludge may be converted to valuable products e.g. animal feed products (see: U.S. Pat. No. 7,931,806), thus significantly improving the wastewater treatment economics.

Second, wastewater streams exhibit a substantial degree of variation in constituent composition. Diurnal variations, seasonal variations, and variations caused by variability in the upstream manufacturing processes, for example, all have the potential to impact the concentration of organic compounds, inorganic micronutrients, and other wastewater constituents. Depending on the constituent composition of the wastewater stream, a wastewater stream may be more or less suitable as an efficient medium to cultivate microbial cells in aeration basins.

Third, it is frequently observed that filamentous microbial organisms grow in conventional aerated biological wastewater systems, a phenomenon known as filamentous bulking (see: US Patent Application 2011/0139714). The growth of filamentous microbial organisms results in poor separation and poor compaction of the microbial mass during solid-liquid separation in the clarification process, in turn potentially resulting in undesirable carry-over of microbial mass into the effluent, as well as an undesirable loss of waste activated sludge and thus loss of raw material for conversion to valuable products.

Fourth, conventional wastewater treatment practices commonly focus on reducing the total biomass produced to reduce disposal costs. This is often achieved by keeping the cells in the aerobic wastewater treatment system for longer periods of time in order to mineralize them into carbon dioxide in the aeration basins. This ages the cells and results, on average, in lower intracellular protein levels. It is also commonly observed that this method of holding the cells for a long period can result in poorer removal rates of nutrients, especially nitrogen and phosphorus, the concentration of which in many instances must be controlled in the effluent before release in order to meet environmental standards. Furthermore, this approach requires large amounts of oxygen to mineralize the organic compounds, which adds significant cost to wastewater treatment. Reducing the mean cell age (also known as "mean cell residence time" or "MCRT") results in an increased mass of cells that are also younger which, when grown appropriately, have the potential to contain high concentrations of protein and other nutritional components.

Fifth, conventional wastewater treatment methods require the use of substantial amounts of oxygen, which is typically supplied by the operation of an aeration blower; however this adds capital and operational costs.

Additionally, some food-processing-derived wastewaters contain compounds that negatively impact the growth of microorganisms. These compounds are most often derived from the plant materials being processed into the food products and result in poor wastewater treatment and lower so called "mixed liquor suspended solids" (or "MLSS") concentrations versus what would normally be observed.

Thus, there are still significant shortcomings in the conventional methodologies for the production of microbial mass in wastewater treatment operations, limiting the total amounts of recoverable value-added products, and sometimes resulting in effluent contaminated with undesirably high concentrations of nutrients and/or microbial organisms.

SUMMARY

In various embodiments, the present invention provides improved and novel methodologies for the production of microbial biomass using an aqueous wastewater stream as the growth medium. The methods provided are superior in many respects to previously known methods, including for production of nutritional components in the microbial biomass, the limitation of filamentous microbes in the wastewater treatment basins, the reduction in effluent levels of nitrogen and phosphorus, the conversion of microbial biomass into valuable product(s), and the ability to produce valuable product(s) from wastewaters comprising compounds inhibiting microbial growth. Additionally, in various embodiments the present invention provides improved and novel methodologies for enriching the microbial biomass with respect to one or more microbial strains using an aqueous waste stream as a growth medium. Such enrichment permits the production of desired microbial compounds.

Accordingly, in various embodiments, the present invention provides an improved method for growing microbial mass comprising:

(a) providing an aqueous wastewater stream;
(b) determining the concentration of micronutrients selected from the group consisting of aluminum, boron, cobalt, magnesium, manganese, and zinc, and any combination thereof, in the aqueous wastewater stream;
(c) determining the biological oxygen demand (BOD) normalized dose of the micronutrients;
(d) modulating the concentration of at least one micronutrient in the aqueous wastewater stream to provide a micronutrient-modulated aqueous wastewater stream, whereby said micronutrient-modulated aqueous wastewater stream has (i) a BOD normalized dose of aluminum between about 60 mg/day/lb BOD/day and about 285 mg/day/lb BOD/day; (ii) a BOD normalized dose of boron between about 115 mg/day/lb BOD/day and about 300 mg/day/lb BOD/day; (iii) a BOD normalized dose of cobalt between about 50 mg/day/lb BOD/day and about 500 mg/day/lb BOD/day; (iv) a BOD normalized dose of magnesium of at least about 100 mg/day/lb BOD/day; (v) a BOD normalized dose of manganese between about 65 mg/day/lb BOD/day and about 220 mg/day/lb BOD/day; and (vi) a BOD normalized dose of zinc between about 115 mg/day/lb BOD/day and about 275 mg/day/lb BOD/day; and
(e) growing microbial biomass in the micronutrient-modulated aqueous wastewater stream.

The microbial biomass obtained in accordance with the present disclosure is useful as an ingredient to prepare animal feed.

In some embodiments of the present invention, step (b) further comprises determining the concentration of macronutrients nitrogen and phosphorus and BOD, wherein the concentration of nitrogen, phosphorus and the BOD is modulated in step (d) to provide: (i) a BOD:nitrogen ratio of at least 100 mg/liter BOD:6-20 mg/liter nitrogen; and (ii) a BOD:phosphorus ratio of at least 100 mg/liter BOD:0.5-2 mg/liter phosphorus.

The concentration of micronutrients, and optionally, macronutrients, may be modulated by increasing the concentration of the micronutrient or, optionally, the macronutrient, or by decreasing the concentration of the micronutrient or, optionally, the macronutrient.

The microbial biomass obtained in accordance with the present disclosure is useful as an ingredient to prepare animal feed.

In some embodiments, the methods provided herein further includes a step (f) comprising diluting a second aqueous wastewater stream with the micronutrient-modulated aqueous wastewater stream obtained after the growing of step (e) to obtain a diluted wastewater stream.

The present invention also provides a composition for use as an additive for the production of microbial biomass comprising a mixture of aluminum, boron, cobalt, magnesium, manganese and zinc, wherein said mixture comprises (i) from about 5.5% to about 28.6% (w/w) aluminum; (ii) from about 4.8% to about 9.1% (w/w) boron; (iii) from about 1.8% to about 9.3% (w/w) cobalt; (iv) from about 9.5% to about 72.7% (w/w) magnesium; (v) from about 7.3% to about 23.9% (w/w) manganese; and (vi) from about 3.6% to about 23.9% (w/w) zinc.

In one of the embodiments of the present invention, the growth of filamentous microorganisms in an aqueous wastewater stream used for the production of microbial biomass is limited. Accordingly, the present invention further provides a method for limiting the growth of filamentous microorganisms in an aqueous wastewater stream used for the production of microbial biomass comprising:

(a) providing an aqueous wastewater stream;
(b) determining the concentration of each of a plurality of micronutrients in the aqueous wastewater stream, the micronutrients including aluminum, boron, calcium, cobalt, magnesium, manganese, and zinc;
(c) determining the biological oxygen demand (BOD) normalized dose of each of the micronutrients;
(d) modulating the concentration of at least one micronutrient in the aqueous wastewater stream to obtain a micronutrient-modulated aqueous waste stream, whereby the micronutrient-modulated aqueous waste stream has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day; and
(e) growing microbial biomass using the micronutrient-modulated aqueous wastewater streams.

In certain aspects, the present invention provides a micronutrient modulated wastewater stream characterized by a settled sludge volume (SSV) which is lower when modulated with at least one micronutrient in such a manner that a micronutrient-modulated aqueous waste stream is obtained that has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day; versus the SSV of wastewater collected from a non-modulated aqueous waste stream.

Furthermore, in certain aspects, the present invention provides a micronutrient modulated wastewater stream characterized by an SSV which is lower than that from the wastewater collected from the same waste stream one to three or more mean cell residence times (MCRTs) after micronutrient-modulation. Furthermore, in accordance with the methods of the present invention, the modulation of the wastewater with at least one micronutrient, results in a decrease in visually observable microbiological filaments in the aqueous wastewater stream.

Accordingly, the aqueous wastewater stream is modulated in such a manner that a micronutrient-modulated aqueous waste stream is obtained wherein (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day, and wherein the modulation results in a decrease in visually observable microbiological filaments in the aqueous wastewater stream.

In some embodiments, the concentration of the macronutrients nitrogen and phosphorus is additionally determined and modulated. Accordingly, the present invention further provides a method for growing microbial mass comprising:
(a) providing an aqueous wastewater stream;
(b) determining the concentration of a plurality of micronutrients in the aqueous wastewater stream, the micronutrients including aluminum, boron, calcium, cobalt, magnesium, manganese, and zinc, and determining the concentration of the macronutrients nitrogen and phosphorus in the aqueous wastewater stream;
(c) determining the biological oxygen demand (BOD) normalized dose of one or more of the micronutrients, including any combination thereof;
(d) modulating the concentration of at least one micronutrient in the aqueous wastewater stream to provide a micronutrient-modulated aqueous wastewater stream, whereby the micronutrient-modulated aqueous wastewater stream has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; (vi) and a BOD normalized dose of zinc of between about 115 mg/day/lb BOD/day and about 275 mg/day/lb BOD/day; and modulating the concentration of at least one macronutrient in the micronutrient-modulated aqueous wastewater stream to provide a micronutrient-modulated and macronutrient-modulated wastewater stream, whereby the micronutrient-modulated and macronutrient-modulated wastewater stream has (vii) a BOD:nitrogen ratio of at least about 100 mg/liter BOD:6-20 mg/liter nitrogen; and (viii) a BOD:phosphorus ratio of at least about 100 mg/liter BOD:0.5-2 mg/liter phosphorus; and
(e) growing microbial biomass using the micronutrient-modulated and macronutrient-modulated aqueous wastewater stream.

In some embodiments of the present invention, a BOD:phosphorus ratio in the micronutrient- and macronutrient-modulated aqueous waste stream following growth of microbial biomass is achieved of about 100 mg/liter BOD:1 mg/liter phosphorus, and a BOD:nitrogen ratio is achieved of about 100 mg/liter BOD:10 mg/liter nitrogen.

The present invention further provides methods for enriching the microbial biomass with respect to one or more microbial strains using an aqueous waste stream as a growth medium. Accordingly, the present invention provides methods for growing a microbial community for the production of microbial biomass comprising the steps of:

(a) providing an aqueous waste stream;
(b) obtaining a microbial community sample comprising a plurality of microbial strains from the waste stream;
(c) growing the plurality of microbial strains of the microbial community under a plurality of growing regimens using the aqueous waste stream as a substrate to produce microbial mass;
(d) determining, in the produced microbial mass, the proportional representation of one or more microbial strains, or one or more cellular constituents produced thereby, capable of producing waste activated sludge compounds in the microbial mass;
(e) determining, in the produced microbial mass, the proportional representation of one or more microbial strains, or one or more cellular constituents produced thereby, capable of producing waste activated sludge compounds in the microbial mass; and
(f) growing the microbial community using the aqueous waste stream as a substrate under the selected growing regimen for the production of waste activated sludge.

In some embodiments, the growing regimens are varied with respect to the concentration of micronutrients. Accordingly, the disclosure further provides:
(a) providing an aqueous waste stream;
(b) obtaining a microbial community sample comprising a plurality of microbial strains from the aqueous waste stream;
(c) growing the plurality of microbial strains of the microbial community under a plurality of growing regimens using the aqueous waste stream as a substrate to produce microbial mass, wherein the BOD normalized dose in the growth medium of (i) aluminum is between about 60 mg/day/lb BOD/day and about 285 mg/day/lb BOD/day; (ii) boron is between about 115 mg/day/lb BOD/day and about 300 mg/day/lb BOD/day; (iii) cobalt is between about 50 mg/day/lb BOD/day to about 500 mg/day/lb BOD/day; (iv) magnesium is at least about 100 mg/day/lb BOD/day; (v) manganese is in the range of between about 65 mg/day/lb BOD/day and about 220 mg/day/lb BOD/day; (vi) zinc is between about 115 mg/day/lb BOD/day and about 275 mg/day/lb BOD/day;
(d) determining, in the produced microbial mass, the proportional representation of one or more microbial strains, or one or more cellular constituents produced thereby, capable of producing waste activated sludge compounds in the microbial mass;
(e) selecting a growing regimen of the plurality of growing regimen under which the proportional representation of the one or more microbial strains in the microbial mass, or the one or more cellular constituents produced thereby, is modulated; and
(f) growing the microbial community using the aqueous waste stream as a substrate under the selected growing regimen for the production of microbial biomass.

In some embodiments, in step (c), additionally the concentration of nitrogen in the growth medium is selected such that the BOD:nitrogen ratio in the growth medium is at least 100 mg/liter BOD:6-20 mg/liter nitrogen, and the concentration of phosphorus in the growth medium is selected such that the BOD:phosphorus ratio is at least 100 mg/liter BOD:0.5-2 mg/liter phosphorus.

In some embodiments, the method further includes a step (g) comprising diluting a second aqueous wastewater stream with the micronutrient-modulated aqueous wastewater stream obtained after the growing of step (e) to obtain a diluted wastewater stream.

In some embodiments, the microbial strain of which the proportional representation is modulated in step (e) is a microbial strain capable of producing a desirable cellular compound, such as protein, crude fat, fatty acid, Coenzyme Q10, nucleic acids, or an amino acid.

Other features and advantages of the present invention will become apparent from the following detailed description. It should be understood, however, that the detailed description and the specific examples, while indicating particular embodiments of the disclosure, are given by way of illustration in a non-limiting manner, since various changes and modifications within the spirit and scope of the disclosure will be apparent to those of skill in the art from the detailed description.

DETAILED DESCRIPTION

Figure 1:
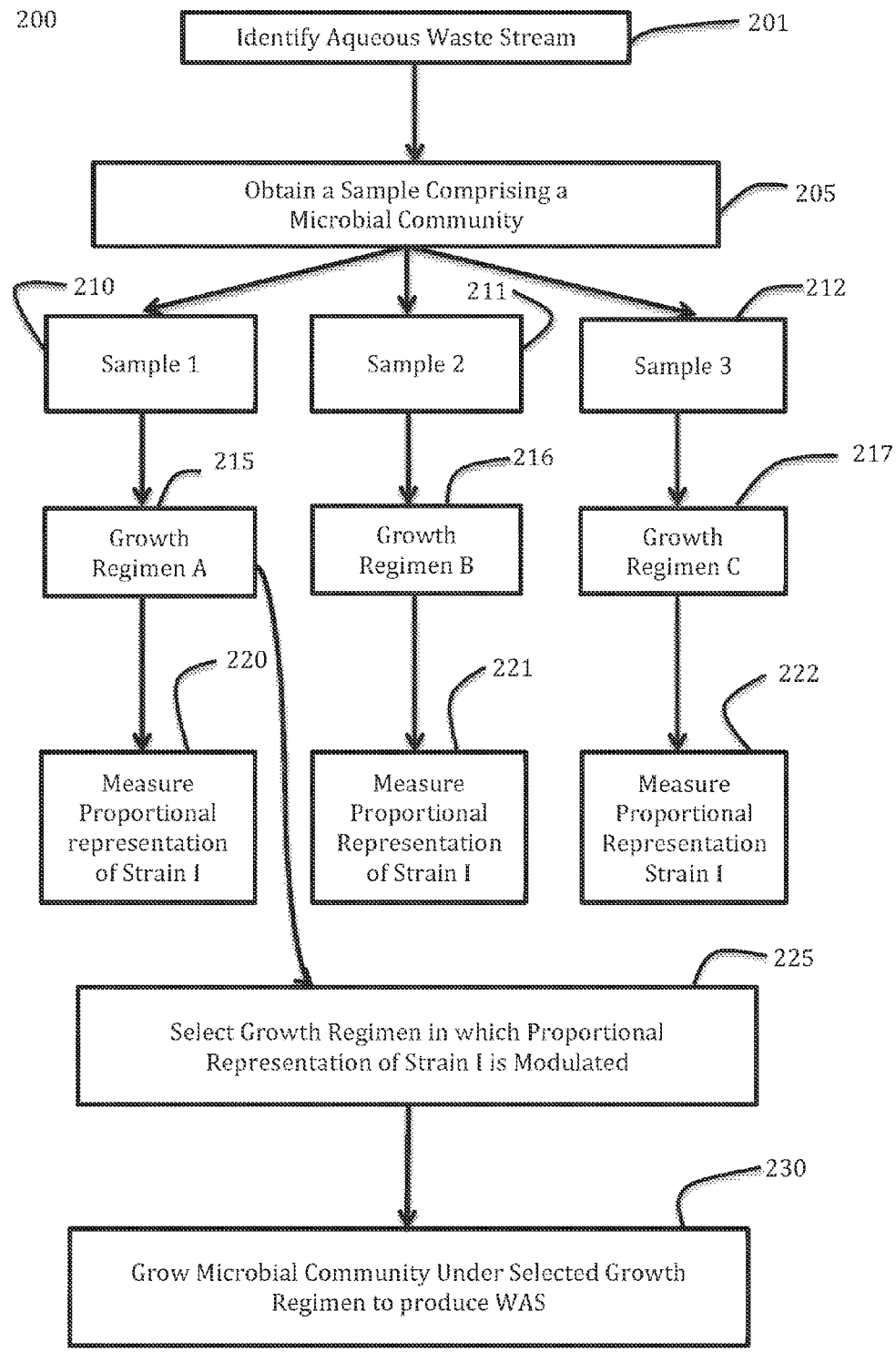
FIG. 1. depicts a flowchart illustrating a method for growing a microbial community to produce waste activated sludge in accordance with one embodiment.

The present invention relates to methods and compositions for the production of microbial biomass from aqueous waste streams. Accordingly, the present disclosure provides methods and compositions for the production of microbial biomass using the aqueous waste stream as a growth medium and adjusting the concentration of certain micronutrients and, optionally, macronutrients in the growth medium. The methods and compositions provided herein are beneficial in that they, surprisingly, result in a significant increase in the total protein in the microbial biomass, which in turn enhances the nutritional value of feed products that may be manufactured from the microbial biomass produced in accordance with the methods set forth herein. The methods of the present invention also result in a reduction in filamentous bulking, and further effect a reduction in the total nitrogen and total phosphorus concentration in the effluent. Additionally, the methods provided herein permit the effective treatment of wastewaters that contain inhibitory concentrations of anti-microbial compounds. Aspects of this disclosure are beneficial for the adjustment in concentration in micronutrients, and optionally macronutrients, to improve the production of protein within the microbial mass of wastewater treatment plants.

Aspects of this disclosure are additionally beneficial for providing micronutrient combinations and concentrations to limit the production of filamentous microorganisms in wastewater treatment plants. Aspects of this disclosure are additionally beneficial for enabling treated effluent from a wastewater treatment plant to be returned to the headworks in order to dilute the source wastewater. The methods provided herein are further advantageous in that they provide for improved settling of microbial mass during the clarification steps of the wastewater treatment process, resulting in turn in a cleaner effluent and improved water remediation, as well as an improved waste activated sludge product.

Accordingly, in various embodiments, the present invention provides an improved method for growing microbial mass comprising:

(a) providing an aqueous wastewater stream;
(b) determining the concentration of micronutrients selected from the group consisting of aluminum, boron, cobalt, magnesium, manganese, and zinc, and any combination thereof, in the aqueous wastewater stream;
(c) determining the biological oxygen demand (BOD) normalized dose of the micronutrients;
(d) modulating the concentration of at least one micronutrient in the aqueous wastewater stream to provide a micronutrient-modulated aqueous wastewater stream, whereby said micronutrient-modulated aqueous wastewater stream has (i) a BOD normalized dose of aluminum between about 60 mg/day/lb BOD/day and about 285 mg/day/lb BOD/day; (ii) a BOD normalized dose of boron between about 115 mg/day/lb BOD/day and about 300 mg/day/lb BOD/day; (iii) a BOD normalized dose of cobalt between about 50 mg/day/lb BOD/day and about 500 mg/day/lb BOD/day; (iv) a BOD normalized dose of magnesium of at least about 100 mg/day/lb BOD/day; (v) a BOD normalized dose of manganese between about 65 mg/day/lb BOD/day and about 220 mg/day/lb BOD/day; and (vi) a BOD normalized dose of zinc between about 115 mg/day/lb BOD/day and about 275 mg/day/lb BOD/day; and
(e) growing microbial biomass in the micronutrient-modulated aqueous wastewater stream Terms and Definitions All documents, including patents, patent applications, and other publications, cited herein are incorporated by reference in their entirety for all purposes. A citation of any document is not to be construed as an admission that it is prior art. Unless defined otherwise, all technical and scientific terms used herein have the same meaning as commonly understood by one of ordinary skill in the art to which the invention pertains.

It is further noted that, as used in this specification and the appended claims, the singular forms "a", "an", and "the" include plural referents unless the content clearly dictates otherwise.

As used herein the following terms shall have the following meanings:

The terms "activated sludge", "waste activated sludge", "WAS", "cellular mass", "bacterial mass", and "bacterial cellular mass" are used interchangeably herein to refer to a more or less concentrated mass of microorganisms obtained or obtainable from a wastewater treatment system.

The terms, "metabolizable component" and "carbon-containing compound" are used interchangeably herein to refer to organic compounds that enable a microorganism to live and grow.

The term "nutrient" as used herein refers to organic and inorganic compounds that enable a microorganism to live and grow.

The term "modulated" as used herein means that the level of a nutrient in a volume is altered by adding mass of that nutrient to that volume in such a manner that the amount of nutrient per unit volume increases, or by removing mass of that nutrient from that volume in such a manner that the amount of nutrient per unit volume decreases, or both.

The term "WWTP" as used herein refers to a wastewater treatment plant.

The term "micronutrient", as used herein, refers to chemical elements and compounds that are required at concentrations not exceeding 100 parts per million for microbial growth and metabolism, and include, but are not limited to, aluminum, boron, cobalt, magnesium, manganese and zinc.

The term "macronutrient" as used herein refers to the chemical elements nitrogen and phosphorus, as well as nitrogen and phosphorus containing compounds, including (but not limited to), for example, urea and phosphoric acid.

The terms "return activated sludge" or "RAS", and "mixed liquor suspended solids" or "MLSS" as used herein refer to certain aspects of microorganism growth in a waste water treatment system. Notably, RAS refers to the proportion of microorganisms that are removed from a waste water system and returned thereto for further growth, including through a process of separation and clarification, and MLSS refers to the total amount of microorganisms residing in a wastewater treatment reservoir, including an aerobic treatment basin.

The terms "total phosphorus" and "total nitrogen" refer to the total concentration of these respective two chemical elements at any given point in a wastewater treatment system, whether in elemental or compound form.

The terms "biological oxygen demand", "BOD", and "$BOD_5$", as used herein interchangeably, refer to the quantity of oxygen required to degrade (or oxidize) contaminants in wastewater biologically. "$BOD_5$" refers to the quantity of oxygen required to degrade contaminants in wastewater biologically in a 5-day period. In general, the BOD correlates with the quantity of material present in wastewater that is available to a microorganism. In some embodiments, the aqueous waste stream comprises a $BOD_5$ of at least about 200 mg per liter of food by-product and residual contaminants.

The term "BOD normalized dose" as used herein in connection with an aqueous wastewater stream refers to the amount of a micronutrient in an aqueous wastewater stream per unit time normalized to the amount of BOD per unit time in such wastewater stream. The BOD normalized dose may be expressed in any appropriate units, including "mg/day/lb BOD/day" which refers to milligram per day per pound of BOD per day.

The term "flow rate", as used herein refers to the volume of aqueous wastewater stream which passes through a given surface in a unit time, and is expressed in volume per unit time, e.g. liter/day or gallon/day.

The term "chemical oxygen demand" or "COD" as used herein interchangeably refer to the quantity of oxygen required to degrade (or oxidize) fully the contaminants in wastewater chemically. In general, the COD correlates with the quantity of material present in wastewater that is able to be oxidized.

The term "MCRT" as used herein refers to the mean cell residence time, or the mean age of microbial cells within a WWTP.

The term "hydraulic residence time" as used herein refers to the residence time of water in the aerobic basin of a WWTP.

The term "washing out" as used herein refers to operating conditions in a WWTP under which settling of microbial cells in the WTTP occurs at a lower rate than the rate at which microbial cells exit the WWTP. Under such conditions the MLSS in the WWTP decreases.

The terms "aqueous wastewater", "aqueous wastewater stream", "waste stream", "wastewater stream", and "wastewater" as interchangeably used herein refer to any wastewater effluent including any effluent from industrial manufacturing processes, municipal, commercial and domestic sources, and runoff water from rainfall or flooding. The wastewater streams used in accordance with the present disclosure include wastewater streams obtained from manufacturing processes of food for human consumption, including wastewater streams comprising food by-products and residuals which require the removal of such food by-products and residuals prior to release into the open environment, and further include, without limitation, wastewater streams relating to beverage production processes, including beer breweries, distilleries, palm oil mills, fruit juice production facilities and the like, potato processors, wet corn and rice millers, sugar manufacturers, citrate producers, yeast manufacturers, animal slaughtering and meat rendering processes, dairy production, and other food production processes that release food-grade biological oxygen demand into effluent water. In some embodiments, the aqueous wastewater stream is a wastewater stream obtained from a beer brewery. Such wastewater stream is characterized by generally comprising highly soluble BOD generally in a range between 500-3000 mg/L with a BOD:COD ratio equal 0.5 or more and most often equal to 0.6-0.7. The main components of brewery BOD are sugars and soluble starches derived from the grain mashing process. In addition, ethanol from the fermentation process is present in low concentration as are soluble fatty acids. The ratio of sugars to starch is higher in brewery wastewaters versus those in a potato or corn processors' wastewaters because the mashing process converts the starches to sugars.

It is further noted that the terms as used herein may refer to volumes of wastewater prior to the production of microbial mass, as well as to volumes of wastewater following the production of one or more MCRTs of microbial mass, as the context requires.

The terms "aluminum", "boron", "cobalt", "magnesium", "manganese", "molybdenum" and "zinc" refer to the respective chemical elements known by these names. In accordance herewith these elements may be provided in their elemental form, as well as in the form of salts or compounds thereof, and furthermore may be complexed in a variety of ways. For example, they may be chelated, using e.g. citric acid or ethylenediaminetetraacetic acid ("EDTA"), to form aluminum EDTA, boron EDTA, cobalt EDTA, magnesium EDTA, manganese EDTA, molybdenum EDTA or cobalt EDTA, etc.

The terms "phosphorus" and "nitrogen" refer to the respective chemical elements known by these names. In accordance herewith these elements may be provided in their elemental form, as well as in the form of salts or compounds thereof, and further may be provided as part of a more complex molecular structure. Thus nitrogen, for example, may be provided in the form of ammonia or urea, and phosphorus may be provided in the form of phosphate.

The term "animal feed" as used herein refers to any composition that may be used as a source of nutrition by a non-human animal, including, but not limited to livestock, including, but not limited to cattle, hog and poultry, companion animals, including but not limited to cats and dogs, as well as aquatic animals, including fin-fish and non-vertebrate aquatic animals including, but not limited to, crustaceans, including but not limited to shrimp, prawns and lobsters.

General Implementation

In accordance with the present invention, an aqueous wastewater stream is provided and the concentration of at least one micronutrient and the BOD normalized dose of at least one micronutrient in the aqueous waste stream are determined. Upon the determination of each of the concentration and the BOD normalized dose, the concentration of the micronutrient in the aqueous wastewater stream is modulated in such a manner that the BOD normalized dose of the micronutrient in the aqueous waste stream is optimized.

Methods to determine the concentrations of micronutrients in an aqueous solution are generally known to the art and may vary. Such methods in general include techniques such as inductively coupled plasma spectroscopy, atomic absorption spectroscopy, ion chromatography, wet chemistry spectrophotometer methods, and colorimetric assays. A variety of inorganic techniques are applicable to the measurement of trace elements in wastewater. Some of these methods include flame atomic absorption spectrometry and graphite furnace (or electrothermal) atomic absorption spectrometry (GFAAS or ETAAS), Laser-Induced Breakdown Spectroscopy (LIBS), inductively coupled plasma optical emission spectrometry (ICP-OES, ICP-AES) and inductively coupled plasma mass spectrometry (ICP-MS). Spectrophotometry methods are also applicable in some instances.

Exemplary specific methodologies to determine the concentration of aluminum in accordance herewith that may be used are further detailed in:
1. Inductively Coupled Plasma-Atomic Emission Spectrometry as described in EPA Method 200.7, "Determination of Metals and Trace Metals in Water and Wastes by Inductively Coupled Plasma-Atomic Emission Spectrometry," http://www.epa.gov/waterscience/methods/method/files/200_7.pdf
2. Laser-Induced Breakdown Spectroscopy as described by Zhijiang Chen, Hongkun Li, Fang Zhao and Runhua Li, *J. Anal. At. Spectrom.*, 2008, 23, 871-875
3. Atomic Absorption Spectroscopy methods and others described in Standard Methods for the Examination of Water and Wastewater, Part 3000 Metals. $22^{nd}$ edition, E. U. Rice et. al, editors. 2012. *American Public Health Association, American Water Works Association, Water Environment Federation*, publishers. Washington, D.C. USA).
4. Hach Spectrophotometer methods 10215 TNT plus, 8012, and 8326 Eriochriome cyanine R. www.Hach.com.

Exemplary specific methodologies to determine the concentration of boron in accordance herewith that may be used are further detailed in:
1. Inductively Coupled Plasma-Atomic Emission Spectrometry as described in EPA Method 200.7, "Determination of Metals and Trace Metals in Water and Wastes by Inductively Coupled Plasma-Atomic Emission Spectrometry," http://www.epa.gov/waterscience/methods/method/files/200_7.pdf
2. Laser-Induced Breakdown Spectroscopy as described by Zhijiang Chen, Hongkun Li, Fang Zhao and Runhua Li, *J. Anal. At. Spectrom.*, 2008, 23, 871-875
3. Atomic Absorption Spectroscopy methods and others described in Standard Methods for the Examination of Water and Wastewater, Part 3000 Metals
4. Spectrophotometric methods such as Hach's Carmine methods 10252 and 8015 Carmine (www.hach.com).

Exemplary specific methodologies to determine the concentration of cobalt in accordance herewith that may be used are further detailed in:
1. Inductively Coupled Plasma-Atomic Emission Spectrometry as described in EPA Method 200.7, "Determination of Metals and Trace Metals in Water and Wastes by Inductively Coupled Plasma-Atomic Emission Spectrometry," http://www.epa.gov/waterscience/methods/method/files/200_7.pdf
2. Laser-Induced Breakdown Spectroscopy as described by Zhijiang Chen, Hongkun Li, Fang Zhao and Runhua Li, *J. Anal. At. Spectrom.*, 2008, 23, 871-875
3. Atomic Absorption Spectroscopy methods and others described in Standard Methods for the Examination of Water and Wastewater, Part 3000 Metals. $22^{nd}$ edition, E. U. Rice et. al, editors. 2012. *American Public Health Association, American Water Works Association, Water Environment Federation*, publishers. Washington, D.C. USA).
4. Spectrophotometric methods such as Hach's method 8078 (www.hach.com).

Exemplary specific methodologies to determine the concentration of magnesium in accordance herewith that may be used are further detailed in:
1. Inductively Coupled Plasma-Atomic Emission Spectrometry as described in EPA Method 200.7, "Determination of Metals and Trace Metals in Water and Wastes by Inductively Coupled Plasma-Atomic Emission Spectrometry," http://www.epa.gov/waterscience/methods/method/files/200_7.pdf
2. Laser-Induced Breakdown Spectroscopy as described by Zhijiang Chen, Hongkun Li, Fang Zhao and Runhua Li, *J. Anal. At. Spectrom.*, 2008, 23, 871-875
3 Atomic Absorption Spectroscopy methods and others described in Standard Methods for the Examination of Water and Wastewater, Part 3000 Metals. $22^{nd}$ edition, E. U. Rice et. al, editors. 2012. *American Public Health Association, American Water Works Association, Water Environment Federation*, publishers. Washington, D.C. USA).

Exemplary specific methodologies to determine the concentration of manganese in accordance herewith that may be used are further detailed in:
1. Inductively Coupled Plasma-Atomic Emission Spectrometry as described in EPA Method 200.7, "Determination of Metals and Trace Metals in Water and Wastes by Inductively Coupled Plasma-Atomic Emission Spectrometry," http://www.epa.gov/waterscience/methods/method/files/200_7.pdf
2. Laser-Induced Breakdown Spectroscopy as described by Zhijiang Chen, Hongkun Li, Fang Zhao and Runhua Li, *J. Anal. At. Spectrom.*, 2008, 23, 871-875
3. Atomic Absorption Spectroscopy methods and others described in Standard Methods for the Examination of Water and Wastewater, Part 3000 Metals. $22^{nd}$ edition, E. U. Rice et. al, editors. 2012. *American Public Health Association, American Water Works Association, Water Environment Federation*, publishers. Washington, D.C. USA).
4. Spectrophotometric methods such as Hach's methods 8034 periodate oxidation, 8034, 8149 PAN, and 8149.

Exemplary specific methodologies to determine the concentration of zinc in accordance herewith that may be used are further detailed in:
1. Inductively Coupled Plasma-Atomic Emission Spectrometry as described in EPA Method 200.7, "Determination of Metals and Trace Metals in Water and Wastes by Inductively Coupled Plasma-Atomic Emission Spectrometry," http://www.epa.gov/waterscience/methods/method/files/200_7.pdf
2. Laser-Induced Breakdown Spectroscopy as described by Zhijiang Chen, Hongkun Li, Fang Zhao and Runhua Li, *J. Anal. At. Spectrom.*, 2008, 23, 871-875
3. Atomic Absorption Spectroscopy methods and others described in Standard Methods for the Examination of Water and Wastewater, Part 3000 Metals. $22^{nd}$ edition, E. U. Rice et. al, editors. 2012. *American Public Health Association, American Water Works Association, Water Environment Federation*, publishers. Washington, D.C. USA).

4. Spectrophotometric methods such as Hach's method 8009 (www.hach.com)

Methods to determine the BOD concentration in an aqueous waste stream are generally known to the art and may vary. The most common methods are described in Standard Methods for the Examination of Water and Wastewater 2012. E. W. Rice, R. B. Baird, A. D. Eaton, and L. S. Clesceri. Other methods exist including pressure sensor instrumentation such as those marketed under the brand name OxiTop®.

Upon having determined the BOD, the BOD normalized dose for a micronutrient in accordance with the present invention is determined. This can be achieved by (a) measuring the flow rate of the aqueous waste stream; (b) calculating the dose per unit time of a micronutrient present in the aqueous wastewater stream; (c) calculating the dose per unit time of BOD present in the aqueous wastewater stream; and (d) calculating the BOD normalized dose for a micronutrient present in the aqueous wastewater stream by dividing the dose per unit time of a micronutrient in the aqueous wastewater stream by the dose per unit time of the BOD.

Methods to measure the flow rate that may be used vary and include paddlewheels, turbines, rotameters, spring and piston devices, positive displacement devices, ultrasonic meters, and magnetic flow meters. A Parshall flume may also be used to measure flow in many instances. In some embodiments, a flow meter is placed within a pipe or open channel and used to measure the flow rate. The flow rate value is sent by electronic signal to a programmable logic controller, computer, or control unit that recalculates the micronutrient or macronutrient addition rate on a regular interval. For example, the flow meter can be programmed to send a new value for flow to the receiving device every second, minute, or desired interval. The receiving unit can automatically then input the flow value into an equation that normalizes the macro- or micronutrient dose. The pumps controlling these macro- or micronutrient sources are then automatically sped up or slowed down to stay within the desired BOD normalized dose range. In the instance where the flow meter does not or cannot send a signal regarding the rate of flow to a receiving device, the value for flow must be read from the meter and inputted manually into the unit controlling the nutrient pumps' rates.

Accordingly, the present invention further provides a method for growing microbial mass comprising:
(a) providing an aqueous wastewater stream;
(b) determining the concentration of micronutrients selected from the group consisting of aluminum, boron, cobalt, magnesium, manganese, and zinc, and any combination thereof, in the aqueous wastewater stream;
(c) determining the BOD concentration in the aqueous wastewater stream
(d) determining the flow rate of the aqueous wastewater stream;
(e) calculating the BOD normalized dose for a micronutrient selected from aluminum, boron, magnesium, manganese, and zinc, and any combination, in the aqueous wastewater stream, using the concentration of the micronutrient, the BOD concentration and the flow rate;
(f) modulating the concentration of at least one micronutrient in the aqueous wastewater stream in such a manner that a micronutrient-modulated aqueous wastewater stream is obtained wherein (i) the BOD normalized dose aluminum varies between about 60 mg/day/lb BOD/day and about 285 mg/day/lb BOD/day; (ii) the BOD normalized dose of boron varies between about 115 mg/day/lb BOD/day and about 300 mg/day/lb BOD/day; (iii) the BOD normalized dose of cobalt varies between about 50 mg/day/lb BOD/day and about 500 mg/day/lb BOD/day; (iv) the BOD normalized dose of magnesium is at least about 100 mg/day/lb BOD/day; (v) the BOD normalized dose of manganese varies between about 65 mg/day/lb BOD/day and about 220 mg/day/lb BOD/day and (vi) the BOD normalized dose of zinc varies between about 115 mg/day/lb BOD/day and about 275 mg/day/lb BOD/day; and
(g) using the micronutrient-modulated aqueous wastewater stream to grow microbial biomass.

Thus, by way of example, an aqueous wastewater stream may be provided and the concentration of aluminum in the wastewater stream may be measured to be 0.02 mg/l. The BOD concentration in the wastewater stream may be measured to be 400 mg/l. The flow rate of an aqueous wastewater stream may be measured to be $2 \times 10^6$ gallons/day (equating to $7.58 \times 10^6$ l/day). From these measurements the aluminum dose in the aqueous wastewater stream may be calculated to be $0.02 \times 7.58 \times 10^6 = 151,600$ mg/day; the BOD dose may be calculated to be $7.58 \times 10^6 \times 400$ mg/day$=3.302 \times 10^9$ mg/day, equating to 6,685 lb/day (1 kg=2.2046 lb); and the BOD normalized dose of aluminum in the wastewater stream may be calculated to be $151,600/6,685=22.68$ mg/day/lb BOD/day. In accordance herewith the concentration aluminum may be adjusted in such a manner that the BOD normalized dose for aluminum is, for example, 100 mg/day/lb BOD/day. Thus the concentration aluminum is modulated by increasing the BOD normalized dose of aluminum by 77.32 mg/day/lb BOD/day. At a flow rate of $2 \times 10^6$ gallons l/day and a BOD of 400 mg/l, the concentration of aluminum in the wastewater stream is increased from 0.02 mg/l to 0.087 mg/l.

It is noted that, in accordance with certain embodiments the determination of the concentration of the micronutrient, the concentration of BOD and the flow rate may be performed in an iterative manner. Thus the present invention further includes embodiments involving the performance of a plurality of measurements for example 1 time per hour, 2 times per hour, or 3 times per hour, to determine the concentration of the micronutrient, the concentration of the BOD and the flow rate. In other embodiments a plurality of measurements is performed in such a manner that measurements are performed substantially continuously, for example, one measurement per second.

Furthermore, measurements and calculations may be implemented in an automated fashion, for example, in such a manner that measurement data is collected and provided to, for example, a computer station for calculation. Automation is particularly preferred in embodiments hereof where continuous measurements are performed. In the foregoing embodiments, upon having performed the measurements, the concentration of the micronutrient may be modulated. Such modulation may be implemented manually upon having evaluated the data, or modulation may additionally be automated, by implementing a computer controlled dispensing means for the micronutrients. The frequency of modulation of the micronutrient may vary. The frequency of modulation of the concentration of micronutrients may be identical to the frequency of the measurements, or may be different, for example, modulation (i.e. adjustment of the concentration of micronutrient) may be performed upon averaging a plurality of BOD normalized doses obtained from a plurality of BOD and micronutrient concentration and flow rate measurements.

In the foregoing manner, fluctuations in the micronutrient concentration in a wastewater stream produced by a wastewater plant, which may vary as a function of time, may be adjusted, and controlled in such a manner that the concentration of the micronutrient in the wastewater stream does not fluctuate outside the herein described ranges, and stays more or less constant as a function of time. In accordance with the foregoing, the present invention further includes a method for growing microbial mass comprising:

(a) providing an aqueous wastewater stream;
(b) determining the concentration of one or more micronutrients selected from the group consisting of aluminum, boron, calcium, cobalt, magnesium, manganese, and zinc in the aqueous wastewater stream at one or more separate time points during a first time interval;
(c) determining the biological oxygen demand (BOD) normalized dose of the micronutrients in the aqueous wastewater stream at one or more separate time points during a second time interval;
(d) modulating the concentration of at least one micronutrient in the aqueous wastewater stream to provide a micronutrient-modulated aqueous wastewater stream, whereby the micronutrient-modulated aqueous wastewater stream has, and maintains during a third time interval, (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day; and
(e) growing microbial biomass using the micronutrient-modulated aqueous wastewater stream.

The first, second and third time interval may each vary in duration and may for example be 1 hr, 2 hrs, 6, hrs, 12 hrs, 1 day, 2, days, 5 days, 20 days or 30 days. The first, second and third time interval may each be different in duration or identical in duration, and the first, second and third time interval may be selected to occur simultaneously or they may be selected to occur at different times. In preferred embodiments, the first, second and third time interval are identical in duration and selected to occur simultaneously. In addition, the number of time points and measurements to determine the micronutrient concentration and the BOD normalized dose of a micronutrient may vary e.g. 2, 5, 10, 20, or 100 time points may be selected in each time interval and the frequency of measurements may vary from e.g. 1/hr, 6/hr, 1/min and 1/s. The measurements of the concentration of micronutrient and the BOD normalized dose of micronutrient may be all conducted at the same time points, or different time points. The frequency of modulation may vary and may e.g. be 1/hr, 2/hr, 1/min or 1/s.

In accordance herewith, the concentration of at least one micronutrient is modulated. Thus, in some embodiments, only the concentration of aluminum, or only the concentration of boron, or only the concentration of cobalt, or only the concentration of magnesium, or only the concentration of manganese or only the concentration of zinc is modulated. In some embodiments, the concentration of at least two micronutrients is modulated. In some embodiments, the concentration of three, four, five, six, or more micronutrients is modulated.

Tables A-F in the Appendix show specific possible combinations and BOD normalized doses of the micronutrients aluminum, boron, cobalt, magnesium, manganese and zinc, that may be modulated in accordance herewith.

Referring to Table A, with respect to aluminum, by way of example, in some embodiments, the BOD normalized dose of aluminum is adjusted to be between about 60 mg/day/lb BOD/day and about 285 mg/day/lb BOD/day.

In some embodiments, the BOD normalized dose of aluminum and one other micronutrient is adjusted so that the BOD normalized dose of aluminum is between about 60 mg/day/lb BOD/day and about 285 mg/day/lb BOD/day; and the BOD normalized dose of boron is between about 115 mg/day/lb BOD/day and about 300 mg/day/lb BOD/day; the BOD normalized dose of aluminum is between about 60 mg/day/lb BOD/day and about 285 mg/day/lb BOD/day; and the BOD normalized dose of cobalt is between about 50 mg/day/lb BOD/day and about 500 mg/day/lb BOD/day; the BOD normalized dose of aluminum is between about 60 mg/day/lb BOD/day and about 285 mg/day/lb BOD/day and the BOD normalized dose of magnesium is about 100 mg/day/lb BOD/day or more; the BOD normalized dose of aluminum is between about 60 mg/day/lb BOD/day and about 285 mg/day/lb BOD/day; and the BOD normalized dose of manganese is between about 65 mg/day/lb BOD/day and about 220 mg/day/lb BOD/day; or the BOD normalized dose of aluminum is between about 60 mg/day/lb BOD/day and about 285 mg/day/lb BOD/day; and the BOD normalized dose of zinc is between about 115 mg/day/lb BOD/day and about 275 mg/day/lb BOD/day.

In some embodiments, the BOD normalized dose of aluminum and two other micronutrients is adjusted so that:
the BOD normalized dose of aluminum is between about 60 mg/day/lb BOD/day and about 285 mg/day/lb BOD/day; the BOD normalized dose of boron is between about 115 mg/day/lb BOD/day and about 300 mg/day/lb BOD/day; and the BOD normalized dose of cobalt is between about 50 mg/day/lb BOD/day and about 500 mg/day/lb BOD/day; or
the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, and the BOD normalized dose of magnesium is 100 mg/day/lb BOD/day or more; or
the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day and the BOD normalized dose of manganese is between about 65 mg/day/lb BOD/day to 220 mg/day/lb BOD/day; or
the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, and the BOD normalized dose of zinc is between about 115 mg/day/lb BOD/day and about 275 mg/day/lb BOD/day; or
the BOD normalized dose of aluminum is between about 60 mg/day/lb BOD/day and about 285 mg/day/lb BOD/day ppm, the BOD normalized dose of cobalt is between about 50 mg/day/lb BOD/day and about 500 mg/day/lb BOD/day, and BOD normalized dose of magnesium is about 100 mg/day/lb BOD/day or more; or the BOD normalized dose of aluminum is between about 60 mg/day/lb BOD/day and about 285 mg/day/lb BOD/day ppm, the BOD normalized dose of cobalt is between about 50 mg/day/lb BOD/day and about 500 mg/day/lb BOD/day and the BOD normalized dose of manganese is between about 65 mg/day/lb BOD/day and about 220 mg/day/lb BOD/day; or the BOD normalized dose of aluminum is between about 60 mg/day/lb BOD/day and about 285 mg/day/lb BOD/day, the BOD normalized dose of cobalt is between about 50 mg/day/lb BOD/day and about 500 mg/day/lb BOD/day, and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of magnesium is about 100 mg/day/lb BOD/day or more and the BOD normalized dose of manganese is between about 65 mg/day/lb BOD/day and about 220 mg/day/lb BOD/day; or the BOD normalized dose of aluminum is between about 60 mg/day/lb BOD/day and about 285 mg/day/lb BOD/day, the BOD normalized dose of magnesium is about 100 mg/day/lb BOD/day or more, and the BOD normalized dose of zinc is between about 115 mg/day/lb BOD/day and about 275 g/day/lb BOD/day.

In some embodiments, the BOD normalized dose of aluminum and three other micronutrients may be adjusted so that:

the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of cobalt is between about 50 mg/day/lb BOD/day and about 500 mg/day/lb BOD/day, and the BOD normalized dose of magnesium is about 100 mg/day/lb BOD/day or more; or the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of cobalt is between about 50 mg/day/lb BOD/day and about 500 mg/day/lb BOD/day, and the BOD normalized dose of manganese is between about 65 mg/day/lb BOD/day and 220 mg/day/lb BOD/day; or the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of cobalt is between about 50 mg/day/lb BOD/day and about 500 mg/day/lb BOD/day and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of magnesium is about 100 mg/day/lb BOD/day or more, and the BOD normalized dose of manganese is between about 65 mg/day/lb BOD/day and about 220 mg/day/lb BOD/day; or the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of magnesium is about 100 mg/day/lb BOD/day or more, and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of manganese is between about 65 mg/day/lb BOD/day and about 220 mg/day/lb BOD/day, and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of cobalt is between about 50 mg/day/lb BOD/day and about 500 mg/day/lb BOD/day, the BOD normalized dose of magnesium is about 100 mg/day/lb BOD/day or more and the BOD normalized dose of manganese is between about 65 mg/day/lb BOD/day and about 220 mg/day/lb BOD/day;

the BOD normalized dose of aluminum is between about 60 mg/day/lb BOD/day and about 285 mg/day/lb BOD/day, the BOD normalized dose of cobalt is between about 50 mg/day/lb BOD/day and about 500 mg/day/lb BOD/day, the BOD normalized dose of magnesium is about 100 mg/day/lb BOD/day or more and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of magnesium is about 100 ppm or more, the BOD normalized dose of manganese is between about 65 mg/day/lb BOD/day to 220 mg/day/lb BOD/day and the BOD normalized dose of zinc is between about 115 mg/day/lb BOD/day and 275 mg/day/lb BOD/day.

In some embodiments, the BOD normalized dose of aluminum and four other micronutrients may be adjusted so that the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of cobalt is between about 50 mg/day/lb BOD/day and about 500 mg/day/lb BOD/day, the BOD normalized dose of magnesium is about 100 mg/day/lb BOD/day or more, and the BOD normalized dose of manganese is between about 65 mg/day/lb BOD/day and about 220 mg/day/lb BOD/day; or the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of cobalt is between about 50 mg/day/lb BOD/day and about 500 mg/day/lb BOD/day, the BOD normalized dose of magnesium is about 100 mg/day/lb BOD/day or more, and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of cobalt is between about 50 mg/day/lb BOD/day and about 500 mg/day/lb BOD/day, the BOD normalized dose of manganese is between about 65 mg/day/lb BOD/day and about 220 mg/day/lb BOD/day, and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of boron is between about 115 mg/day/lb BOD/day about and 300 mg/day/lb BOD/day, the BOD normalized dose of magnesium is about 100 mg/day/lb BOD/day ppm or more, the BOD normalized dose of manganese is between about 65 mg/day/lb BOD/day and about 220 mg/day/lb BOD/day, and the BOD normalized dose of zinc is between about 115 mg/day/lb BOD/day and about 275 mg/day/lb BOD/day; or the BOD normalized dose of aluminum is between about 60 mg/day/lb BOD/day and about 285 mg/day/lb BOD/day, the BOD normalized dose of cobalt is between about 50 mg/day/lb BOD/day and about 500 mg/day/lb BOD/day, the BOD normalized dose of magnesium is about 100 mg/day/lb BOD/day ppm or more, the BOD normalized dose of manganese is between about 65 mg/day/lb BOD/day and about 220 mg/day/lb BOD/day, and the BOD normalized dose of zinc is between about 115 mg/day/lb BOD/day and about 275 mg/day/lb BOD/day.

In some embodiments, the BOD normalized dose of aluminum and five other micronutrients may be adjusted so that the BOD normalized dose of aluminum is between about 60 mg/day/lb BOD/day and about 285 mg/day/lb BOD/day, the BOD normalized dose of boron is between about 115 mg/day/lb BOD/day and about 300 mg/day/lb BOD/day, the BOD normalized dose of cobalt is between about 50 mg/day/lb BOD/day and about 500 mg/day/lb BOD/day, the BOD normalized dose of magnesium is about 100 mg/day/lb BOD/day or more, the BOD normalized dose of manganese is between about 65 mg/day/lb BOD/day and about 220 mg/day/lb BOD/day, and the BOD normalized dose of zinc is between about 115 mg/day/lb BOD/day and about 275 mg/day/lb BOD/day.

It will be clear those of skill in the art that, similarly to the foregoing, Tables B, C, D, E and F are providing adjustments of concentrations boron, cobalt, magnesium, manganese, and zinc, respectively, alone or in combination with 2, 3, 4, 5, or more micronutrients that may be made in accordance with some embodiments of the present invention.

In embodiments where the concentration of more than one micronutrient is modulated, any combination of micronutrients may be modulated. Whether the concentration(s) of one or more micronutrients is (or are) modulated in accordance herewith depends on the concentration of micronutrients that is determined to be present in the aqueous waste stream. Thus, for illustrative purposes, if in an aqueous waste stream it is determined that the concentration of aluminum is 0.01 ppm, the concentration of boron is 0.2 ppm, the concentration of cobalt is 0.2 ppm, the concentration of magnesium is 1.0 ppm, the concentration of manganese is 0.3 ppm, the concentration of zinc is, 0.01 ppm; the average BOD is 700 mg/L, and the flow rate is 2,000,000 gallons/day, then that equates to a BOD normalized dose of the micronutrients of 6 mg Al/day/lb BOD/day, 130 mg B/day/lb BOD/day, 130 mg Co/day/lb BOD/day, 649 mg Mg/day/lb BOD/day, 193 mg Mn/day/lb BOD/day, and 6 mg Zn/day/lb BOD/day, respectively. In accordance herewith, the concentration of aluminum in the aqueous waste stream is modulated by adding aluminum to achieve a BOD normalized dose of aluminum in the aqueous waste stream that is at least about 60 mg/day/lb BOD/day and no more than about 285 mg/day/lb BOD/day, and the BOD normalized dose of zinc in the aqueous waste stream would be modulated to achieve a BOD normalized dose of at least about 115 mg/day/lb BOD/day and not more than about 275 mg/day/lb BOD/day. The concentration of boron, cobalt, magnesium and manganese would not be modulated. Where the concentration of any of the aforementioned micronutrients in the aqueous waste stream is determined to be below the specified concentration range, the concentration is modulated by adding an additional amount of the micronutrients in such a manner that a concentration within the specified range is achieved.

It is further noted that in accordance herewith, the concentration of some micronutrients may be increased while the concentration of others may be reduced. Whether the concentration(s) of one or more micronutrients is (or are) modulated in accordance herewith depends on the concentration of micronutrients that is determined to be present in the aqueous waste stream. Thus, for illustrative purposes, if in an aqueous waste stream it is determined that the concentration of aluminum is 0.01 ppm, the concentration of boron is 0.2 ppm, the concentration of cobalt is 0.2 ppm, the concentration of magnesium is 0.5 ppm, the concentration of manganese is 10 ppm, the concentration of zinc is 0.01 ppm; the average BOD is 700 mg/L; and the flow rate is 2,000,000 gallons/day, then that equates to 6 mg Al/day/lb BOD/day, 130 mg B/day/lb BOD/day, 130 mg Co/day/lb BOD/day, 324 mg Mg/day/lb BOD/day, 6,492 mg Mn/day/lb BOD/day, and 6 mg Zn/day/lb BOD/day. In accordance herewith, the concentration of manganese is reduced, for example through the application of ion exchange or precipitation methodologies, to a BOD normalized dose of between about 65 mg/day/lb BOD/day and about 220 mg/day/lb BOD/day, the concentration of aluminum in the aqueous waste stream is modulated by adding aluminum to achieve a BOD normalized dose of aluminum in the aqueous waste stream that is at least about 60 mg/day/lb BOD/day and no more than about 285 mg/day/lb BOD/day, and the concentration of zinc in the aqueous waste stream would be modulated to achieve a BOD normalized dose of at least about 115 mg/day/lb BOD/day and not more than about 275 mg/day/lb BOD/day. The concentration of boron, cobalt, and magnesium would not be modulated. Where the concentration of any of the aforementioned micronutrients in the aqueous waste stream is determined to be below the specified concentration range, the concentration is modulated by adding an additional amount of the micronutrients in such a manner that a concentration within the specified range is achieved. If the method of micronutrient removal results in a concentration of the micronutrient below the desired concentration of such micronutrient, additional amounts of the micronutrient may be supplied to the aqueous wastewater stream. In some embodiments, a portion of the influent wastewater stream is subjected to micronutrient removal, through e.g. ion exchange, so that the targeted concentration can be achieved without having to add the micronutrient after its removal. For example, if there is 33% excess of a micronutrient in the influent wastewater, 33% of the wastewater flow needs to be subjected to a removal process with an efficiency approaching 100%. After the micronutrient is removed from the 33% wastewater flow, the other two-thirds of the wastewater flow can be mixed together with the one third treated wastewater flow (thereby, achieving 100% of the original wastewater flow) and achieving a micronutrient concentration equivalent to 100% of the target.

It is further noted that the concentration of magnesium (Mg) in accordance herewith is at least 100 mg/day/lb BOD/day. The upper limit for the concentration of Mg is relatively flexible and may in principle be selected as desired, for example, the BOD normalized dose of Mg may be 200 mg/day/lb BOD/day, or 500 mg/day/lb BOD/day ppm, or 1000 mg/day/lb BOD/day, or 3000 mg/day/lb BOD/day. In some embodiments the concentration of magnesium is determined and modulated if the BOD normalized dose of magnesium in the wastewater stream is less than about 100 mg/day/lb BOD/day.

In some embodiments, aluminum is added in the form of an aluminum salt, such as aluminum sulfate ($Al_2SO_4$), where aluminum is present in the 3+ valence state. However, other salts where aluminum is in the +2 or +1 valence states may also be used. In addition, the aforementioned salts may be hydrated.

In some embodiments, boron is added in the form of boric acid ($H_3BO_3$) or other boron salts where boron is preferably present in the 3+ valence state. Other boron salts containing boron in the 2+ or 1+ valence states may also be used. In addition, the aforementioned salts may be hydrated.

In some embodiments, cobalt is added in the form of a cobalt salt such as cobalt sulfate ($CoSO_4$) or other cobalt salts where cobalt is preferably present in the 2+ valence state. However, other salts containing cobalt in the 5+, 4+, 3+, 1+, or 1− may also be used. In addition, the aforementioned salts may be hydrated.

In some embodiments, magnesium is added in the form of a salt such as magnesium sulfate ($MgSO_4$) or other magnesium salts where magnesium is in the 2+ valence state. However, other oxide forms where magnesium is in the 1+ valence state may also be used. In addition, the aforementioned salts may be hydrated.

In some embodiments, manganese is added in the form of a manganese salt such as manganese sulfate ($MnSO_4$) or other manganese salts, where manganese is present in the 2+ valence state. However, other salts where manganese is present in the 7+, 6+, 5+, 4+, 3+, 1+, 1−, 2−, or 3− valence state may also be used. In addition, the aforementioned salts may be hydrated.

In some embodiments, zinc is added in the form of a zinc salt, such as zinc sulfate ($ZnSO_4$), where zinc is present in the 2+ valence state. Zinc metal in the uncharged valence state is also applicable. In addition, the aforementioned salts may be hydrated.

In accordance herewith micronutrients may be added in liquid form and/or solid form, for example as a powder or in any other form, as appropriate.

In some embodiments, the concentrations of the macronutrients phosphorus and nitrogen are additionally determined and modulated. Accordingly, the present disclosure further provides a method of growing microbial biomass comprising:
(a) providing an aqueous wastewater stream;
(b) determining the concentration of a plurality of micronutrients in the aqueous wastewater stream, the micronutrients including aluminum, boron, calcium, cobalt, magnesium, manganese, and zinc, and determining the concentration of the macronutrients nitrogen and phosphorus in the aqueous wastewater stream;
(c) determining the biological oxygen demand (BOD) normalized dose of one or more of the micronutrients;
(d) modulating the concentration of at least one micronutrient in the aqueous wastewater stream to provide a micronutrient-modulated aqueous wastewater stream, whereby the micronutrient-modulated aqueous wastewater stream has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; (vi) and a BOD normalized dose of zinc of between about 115 mg/day/lb BOD/day and about 275 mg/day/lb BOD/day; and modulating the concentration of at least one macronutrient in the micronutrient-modulated aqueous wastewater stream to provide a micronutrient-modulated and macronutrient-modulated wastewater stream, whereby the micronutrient-modulated and macronutrient-modulated wastewater stream has (vii) a BOD:nitrogen ratio of at least about 100 mg/liter BOD:6-20 mg/liter nitrogen; and (viii) a BOD:phosphorus ratio of at least about 100 mg/liter BOD:0.5-2 mg/liter phosphorus; and
(e) growing microbial biomass using the micronutrient-modulated and macronutrient-modulated aqueous wastewater stream.

Methods to determine the concentrations of macronutrients are generally known to the art and may vary. Such methods in general include techniques such as ion selective probes, colorimetric assays, and spectrophotometer methods.

Exemplary specific methodologies to determine the concentration of nitrogen in water in accordance herewith that may be used are detailed in:

Spectrophotometric methods including total nitrogen by persulfate digestion or titanium trichloride reduction, kjeldahl nitrogen by peroxide digestion, and ammonia by the salicylate and nessler methods. Ammonia and nitrate probes are also applicable. Other applications of the kjeldahl method are also relevant as described in:
1. Standard Methods for the Examination of Water and Wastewater 2012. E. W. Rice, R. B. Baird, A. D. Eaton, and L. S. Clesceri.
2. Metcalf and Eddy Inc. 1991. *Wastewater Engineering: Treatment, Disposal, and Reuse*. Tchobanoglous, G. and Burton F. (eds). Irwin McGraw-Hill: New York; Montréal.

Ionic forms of nitrogen may be measured by ion chromatography.

Specific methodologies to determine the concentration of phosphorus that may be used are detailed in:
1. Spectrophotometric methods including total phosphorus by acid hydrolysis and reactive orthophosphate.
2. Ionic forms of phosphorus may be measured by ion chromatography or ion selective probes.

Specific methodologies to determine the BOD that may be used in accordance herewith are described in Standard Methods for the Examination of Water and Wastewater which is incorporated herein by reference in its entirety (Standard Methods for the Examination of Water and Wastewater, $22^{nd}$ edition, E. U. Rice et. al, editors. 2012. *American Public Health Association, American Water Works Association, Water Environment Federation*, publishers. Washington, D.C. USA). Pressure sensor instrumentation such as those marketed under the brand name OxiTop® is also applicable.

Once the concentration of each of these macronutrients in the aqueous wastewater stream has been determined, the concentration in the aqueous wastewater stream of these macronutrients may be modulated, as required to a concentration in accordance herewith the as follows:
(i) the concentration of nitrogen is adjusted in such a manner that a BOD:nitrogen ratio is achieved of at least 100 mg/liter BOD:6-20 mg/liter nitrogen; and (ii) a BOD:phosphorus ratio is achieved of at least 100 mg/liter BOD:0.5-2.0 mg/liter phosphorus.

For the purpose of clarity, with the term "at least" as used herein in connection with the ratios of BOD:nitrogen and BOD:phosphorus, it is meant that encompassed within these embodiments are ratios that exceed 100 mg/liter BOD:6-20 mg/liter nitrogen, and 100 mg/liter BOD:0.5-2.0 for the BOD:nitrogen and BOD:phosphorus ratios, respectively; thus for example, a ratio of 130 mg/liter BOD:6-20 mg/liter nitrogen, and 130 mg/liter BOD:0.5-2.0 phosphorus are included herein.

In particular embodiments of the present invention, the concentration in the aqueous growth substrate is modulated to achieve the following:

(i) the concentration of nitrogen is adjusted in such a manner that a BOD:nitrogen ratio is achieved of about 100 mg/liter BOD:10 mg/liter nitrogen; and (ii) a BOD:phosphorus ratio is achieved of about 100 mg/liter BOD:1 mg/liter phosphorus.

The concentrations of nitrogen and the concentration of phosphorus may, in accordance herewith, be modulated together with the concentrations of at least one of the micronutrients and further includes modulation of nitrogen and phosphorus together with the micronutrients in any of the combinations set forth in Tables A-F.

Where the concentration of any of the aforementioned macronutrients in the aqueous waste stream is determined to be below the specified concentration range, the concentration is modulated by adding an additional amount of the macronutrients in such a manner that the BOD:macronutrient ratio is reduced to a value within the specified range is achieved.

Where the concentration of any of the aforementioned micronutrients and macronutrients in the aqueous waste stream is determined to be below the specified concentration range, the concentration and the BOD:macronutrient ratio, respectively, are modulated by adding an additional amount of the micronutrients and macronutrients in such a manner that a concentration and BOD:macronutrient ratio, respectively, within the specified range is achieved.

Nitrogen may be added in the form of reduced nitrogen, including in the form of ammonia or ammonia-based compounds, urea, manures or other forms of reduced soluble nitrogen.

Phosphorus may be added in the form of molecular phosphorus, however in some embodiments phosphorus is added in the form of phosphoric acid.

The micronutrients and macronutrients may be contacted directly with the wastewater stream to be treated in accordance herewith, prior to or after the wastewater stream has been collected in a holding tank, reactor or aerobic basin, or the micronutrients and macronutrients may be contacted with recycled bacterial mass prior to the return of such mass to the holding tank, reactor, or aerobic basin or the micronutrients and macronutrients may be added to settling tanks or clarifiers, or any combination thereof. In some embodiments the micronutrients and macronutrients are added into the untreated wastewater together with recycled microbial biomass, also referred to as "return activated sludge" or "RAS", prior to the introduction of the wastewater, recycled microbial biomass, and micronutrients, and optionally, macronutrients, to the aerobic basin.

Where the concentration of the aforementioned micronutrients in the aqueous wastewater stream is determined to be in excess of the specified concentration range, and/or where the BOD:macronutrient ratio is determined to be below the herein specified ratio, such micronutrient or macronutrient may be removed from the aqueous waste stream. Such removal may, for example, be achieved by determining the source of the micronutrient or macronutrient in the industrial production process and adjusting the amount of micronutrient and macronutrient used in the production process, by altering the chemicals used in the production plant such as the detergents, cleaners, or degreasing agent. In addition, micronutrients can be removed from the wastewater deriving from the plant by employing physical and chemical methods of removal such as ion exchange, precipitation, or chelation prior to their introduction to the wastewater treatment plant. Macronutrients additionally may be removed by sequestering such macronutrients into microbial cells and removing such cells. In particular, younger microbial cells are capable of sequestering macro-nutrients. Thus by generating a younger cell population, i.e. a population with a lower MCRT (as further detailed below), and removing cells from the reactor system it is possible to remove macronutrients from the wastewater stream, and increase the BOD:nitrogen and the BOD:phosphorus ratios as desired.

In some embodiments, the pH of the aqueous waste stream is controlled. The pH may be adjusted to be basic or acid or circumneutral (i.e. a pH of about 7.0). Preferably strong acidic and strong basic conditions are avoided, and a pH of the aqueous waste stream ranging from about 5.5 to about 8.5 is preferred. The pH may be adjusted either prior to or following the modulation of the micronutrient, and optionally, macronutrient concentrations in the waste stream.

In some embodiments, growth factors may be contacted with the aqueous waste stream and mixed therewith. Growth factors that may be used in accordance herewith include yeast extracts, which are, for example, added at a concentration of about 1.0 ppm and 100 ppm, molasses, including sorghum molasses, the press water from brewery wort, palm oil mill effluent, and waste products. In some embodiments, growth factors are added to the wastewater stream after the determination of the concentration of micronutrients, and optionally macronutrients to allow final concentrations to be calculated based on the addition of a known amount of the individual growth factor. For example, the micronutrient concentrations of the aqueous waste stream and a palm oil mill effluent can be determined using inductively coupled plasma spectroscopy as explained herein. Knowing these concentrations will allow the calculation of final micronutrient concentrations in the aqueous waste stream when a known amount of palm oil mill effluent is continuously added to the aqueous waste stream.

Once the concentration of the micronutrients and, optionally, the concentration of macronutrients in the aqueous waste stream have been adjusted in accordance with the methodologies hereinbefore described, microbial biomass is grown in accordance with methodologies and techniques generally known to the art and typically involving the steps of (i) microbial proliferation in a growth vessel or reactor, such as an aeration reactor using the micronutrient- and, optionally, macronutrient-modulated aqueous waste stream as a growth medium, (ii) separation of the microbial biomass from the aqueous effluent, using settling tanks, clarifiers, membrane-based separation techniques or other processes and unit operations generally known to the skilled artisan, and (iii) recovering the microbial biomass or waste activated sludge.

In some embodiments, the growth process is carried out under essentially aerobic conditions. The term "essentially aerobic conditions" is intended to refer to conditions where the growth of the microbial biomass under conditions where oxygen supply is controlled by aeration in such a manner that predominant growth of microbial species digesting carbon in an aerobic manner is promoted. While some anaerobic growth may occur, such growth is limited to less than 50%, to less than 25% to less than 10%, and all values in between. Typically in order to achieve essentially aerobic growth conditions a supply of oxygen to the aqueous waste stream in an amount of at least 0.5 ppm, more preferably at least 1-2 ppm is required. The microbial biomass produced under essentially aerobic conditions is also referred to as "aerobic microbial biomass." Two operating parameters that are of particular import are the "mean cell residence time" or "MCRT" and the "mean waste residence time" or "MWRT". The MCRT can be calculated by dividing the total microbial biomass in the wastewater treatment process by the microbial biomass removed per unit time. The total microbial biomass in the process can be measured by various conventional methods, for example by removing samples from the wastewater stream of known volume, measuring the microbial biomass in the samples, and extrapolating the microbial biomass in the samples to the microbial biomass in the total volume present in the process. Thus, by way of example, if the total microbial biomass is 100 pounds, and 20 pounds of microbial biomass is removed per day, the MCRT is 5 days. In some embodiments the MCRT is about 8 days or less. In some embodiments, the MCRT is maintained to be about 7 days, about 6 days, about 5 days, about 4 days, about 3 days or about 2 days. Alternatively stated, no more than ⅛, 1/7, ⅙, ⅕, ¼, ⅓, ½ of the microbial biomass is removed from the process. The MWRT refers to the mean residence time of the carbon containing compounds in the process (e.g. the organic compounds contributing to the BOD of the waste stream), measured from the time at which these compounds enter the process (e.g. the aeration vessel) to the time at which, and ending at the time at which these compounds are recovered from the process in the form of microbial biomass. The MWRT is calculated by dividing the total mass of carbon in the process by the total mass of carbon that is recovered per day. Thus, by way of example, if the total mass of carbon in the process is 100 pounds and 15 pounds of carbon is recovered per day, the MWRT is 6.7 days. In some embodiments the MRWT is about 10 days or less. In some embodiments the MWRT is less than about 8 days, less than about 7 days, less than about 6 days, less than about 5 days, less than about 4 days, less than about 3 days or less than about 2 days. Further guidance on control and optimization of MWRT and MCRT and other operating parameters relating to the growth and recovery of the microbial biomass in accordance herewith additionally may be found in U.S. Pat. No. 7,931,806, which is incorporated herein by reference in its entirety for all purposes. It is noted that the foregoing may be conducted at any scale. In addition, where existing growth reactors or basins are used the volume thereof may be adjusted, either by adding further capacity or by reducing the volume thereof, for example by separating parts of a basin or filling a basin with a solid material, such as sand, rocks or soil. Several of the Examples hereinafter provided show production at laboratory scale. The methods provided herein may be implemented in wastewater treatment plants of any scale or size.

The present invention also provides compositions for use as an additive for the production of bacterial mass comprising a mixture of aluminum, boron, cobalt, magnesium, manganese and zinc, wherein said mixture comprises (i) from about 5.5% to about 28.6% (w/w) aluminum; (ii) from about 4.8% to about 9.1% (w/w) boron; (iii) from about 1.8% to 9.3% (w/w) cobalt; (iv) from about 9.5% to about 72.7% (w/w) magnesium; (v) from about 7.3% to about 23.9% (w/w) manganese; and (vi) from about 3.6% to about 23.9% (w/w) zinc.

In some embodiments, the mixture comprises said mixture comprises about 5.5% aluminum; (ii) about 9.1% (w/w) boron; (iii) about 1.8% (w/w) cobalt; (iv) about 72.7% (w/w) magnesium; (v) about 7.3% (w/w) manganese; and (vi) about 3.6% (w/w) zinc.

In accordance herewith, the foregoing compositions are used as additives to enrich the wastewater stream and modulate the micronutrient concentration therein.

As hereinbefore mentioned, the modulation of micronutrients and, optionally macronutrients, as described herein, surprisingly results in proliferation of predominantly non-filamentous microbial organisms with limited growth of filamentous microorganisms. The relatively low concentration of filamentous microorganisms facilitates separation of the microbial biomass, notably where gravity based separation is used to allow the microbial biomass to settle and separate. Gravitational settling times may conveniently be monitored and quantitated using a settleometer, notably by determining settled sludge volume values (or "SSVs"). This typically involves the use of a special graduated cylinder (called a "settleometer") and measurement of the volume that the sludge (i.e. the microbial biomass) occupies after a specified period of time. Thus the $SSV_{60}$ represents the volume of settled biomass after a period of 60 minutes of settling, and is typically reported in ml/liter. In some embodiments, the $SSV_{60}$ exhibited by the micronutrient-modulated, and optionally macronutrient-modulated wastewater stream, following production of microbial biomass in accordance with the present invention is reduced, when compared with the $SSV_{60}$ of a non-modulated wastewater stream, preferably, the same wastewater stream prior to modulation with the micronutrients, or optionally, the macronutrients. In some embodiments, the $SSV_{60}$ is of the modulated wastewater stream is at least about 10%, less than the $SSV_{60}$ of a non-modulated wastewater stream, or 10% less than the $SSV_{60}$ of the same wastewater stream obtained at least 1, 2 or 3 MCRTs prior to micronutrient-modulation, where all other operating parameters are kept constant. The term "all operating parameters are kept constant" means that the parameters capable of influencing growth in the aqueous wastewater medium, including dissolved oxygen, MCRT, $BOD_5$ load, and flow rates are maintained at the same level as when the micronutrient modulation of the wastewater stream was initiated. Thus, by way of example, if the MCRT of the biomass in a wastewater stream is 10 days, in one aspect the methods of the current invention provide a lower SSV within 10, 20 or 30 days or more of the modulation of the wastewater stream with micronutrients, when all operating parameters are kept constant.

In further preferred embodiments, the $SSV_{60}$ of the modulated wastewater stream is at least about 20%, 30%, 40% or 50% lower when compared to the $SSV_{60}$ of a non-modulated wastewater stream, or when compared to the $SSV_{60}$ of the same wastewater stream obtained at least 1, 2 or 3 MCRTs prior to micronutrient-modulation, where all other operating parameters have been kept constant.

In some embodiments, the $SSV_{60}$ exhibited by the aqueous wastewater stream following the production of microbial biomass in accordance with the here provided methods, is less than about 900 ml/liter. In some embodiments, the $SSV_{60}$ is less than about 800 ml/liter, or less than about 700 ml/liter, or less than about 600 ml/liter, or less than about 500 ml/liter. In some embodiments the $SSV_{60}$ is between about 450 and 550 ml/liter.

In some embodiments, the micronutrient concentrations are adjusted to optimized micronutrient concentration levels. With the term "optimized concentration levels" it is meant that the $SSV_{60}$ is reduced to a level at which production of filamentous microorganisms does not or does not materially interfere with growth of non-filamentous microorganisms. In accordance with this embodiment, the micronutrient concentration is initially modulated in a wastewater stream to achieve a BOD normalized doses of micronutrients set forth in Tables A-F, and the $SSV_{60}$ is measured. Subsequently, the concentration of one or more of the micronutrients is iteratively varied from the selected concentration but in such a manner that the BOD normalized doses of the aqueous waste stream are maintained within the ranges set forth in Tables A-F, and the $SSV_{60}$ of the wastewater is measured at each iteration. Thus, an optimized concentration level of micronutrient may be obtained. The foregoing embodiment may conveniently be implemented using a laboratory scale reactor system described in Example 1 herein. This embodiment is further detailed in Example 10.

In some embodiments, the SSV is lower at any given time when the wastewater stream is modulated with at least one micronutrient in such a manner that a micronutrient-modulated aqueous waste stream is obtained wherein (i) the BOD normalized dose of aluminum varies between about 60 mg/day/lb BOD/day and about 285 mg/day/lb BOD/day; (ii) the BOD normalized dose of boron varies between about 115 mg/day/lb BOD/day and about 300 mg/day/lb BOD/day; (iii) the BOD normalized dose of cobalt varies between about 50 mg/day/lb BOD/day and about 500 mg/day/lb BOD/day; (iv) the BOD normalized dose of magnesium is at least about 100 mg/day/lb BOD/day; (v) the BOD normalized dose of manganese varies between about 65 mg/day/lb BOD/day and about 220 mg/day/lb BOD/day; (vi) and the BOD normalized dose of zinc varies between about 115 mg/day/lb BOD/day and about 275 mg/day/lb BOD/day versus the SSV of the biomass collected from the same non-micronutrient modulated aqueous waste stream, when examined one to three MCRTs prior to micronutrient addition and when other operational conditions including dissolved oxygen, MCRT, $BOD_5$ load, and flow rates remain unchanged from their levels prior to micronutrient addition. For example, if the MCRT of the biomass is 10 days, the current invention provides a lower SSV within 10-30 days of the modulation of the waste stream with micronutrients. Furthermore, the modulation of the wastewater with at least one micronutrient in such a manner that a micronutrient-modulated aqueous waste stream is obtained wherein (i) the BOD normalized dose of aluminum varies between about 60 mg/day/lb BOD/day and about 285 mg/day/lb BOD/day; (ii) the BOD normalized dose of boron varies between about 115 mg/day/lb BOD/day and about 300 mg/day/lb BOD/day; (iii) the BOD normalized dose of cobalt varies between about 50 mg/day/lb BOD/day and about 500 mg/day/lb BOD/day; (iv) the BOD normalized dose of magnesium is at least about 100 mg/day/lb BOD/day (v) the BOD normalized dose of manganese varies between about 65 mg/day/lb BOD/day and about 220 mg/day/lb BOD/day; (vi) and the BOD normalized dose of zinc varies between about 115 mg/day/lb BOD/day and about 275 mg/day/lb BOD/day, provides a decrease in observable filaments in the wastewater stream using microscopy techniques when other operational conditions such as dissolved oxygen, MCRT, $BOD_5$ load, and flow rates are maintained constant.

The present invention further provides a method for limiting the growth of filamentous microorganisms in an aqueous wastewater stream used for the production of microbial biomass comprising:
  (a) providing an aqueous wastewater stream;
  (b) determining the concentration of each of a plurality of micronutrients in the aqueous wastewater stream, the micronutrients including aluminum, boron, calcium, cobalt, magnesium, manganese, and zinc;
  (c) modulating the concentration of at least one micronutrient in the aqueous wastewater stream to obtain a micronutrient-modulated aqueous waste stream, whereby the micronutrient-modulated aqueous waste stream has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day; and
  (d) growing microbial biomass using the micronutrient-modulated aqueous wastewater streams.

As hereinbefore mentioned, the methods provided herein result in the production of a wastewater stream in which the concentration of nitrogen and phosphorus is substantially reduced, thus providing for an aqueous waste stream that more readily meets environmental standards. Accordingly, the present invention further provides:

a method for restricting the concentration of phosphorus and nitrogen in an aqueous wastewater stream used for the production of microbial biomass comprising:
  (a) providing an aqueous wastewater stream;
  (b) determining the concentration of each of a plurality of micronutrients in the aqueous wastewater stream, the micronutrients including aluminum, boron, calcium, cobalt, magnesium, manganese, and zinc;
  (c) determining the biological oxygen demand (BOD) normalized dose of one or more of the micronutrients;
  (d) modulating the concentration of at least one micronutrient in the aqueous wastewater stream to provide a micronutrient-modulated aqueous wastewater stream, whereby the micronutrient-modulated aqueous wastewater stream has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day; and
  (d) growing microbial biomass using the micronutrient-modulated aqueous wastewater stream;
  wherein the concentration of total phosphorus in the micronutrient-modulated aqueous wastewater stream obtained after the growing of step (e) is less than about 1.5 mg/L and the concentration of total nitrogen is less than about 5 mg/L.

As hereinbefore mentioned, the microbial biomass that is obtained in accordance herewith further has a superior constituent quality, rendering it particularly useful as a source material for the manufacture of valuable products. Thus, the microbial biomass obtained in accordance with the present disclosure may be used as an ingredient to prepare an animal feed, or as an additive to compositions known to be useful as an animal feed, notably a feed additive or nutrient to enhance the nutritional value of known feed compositions. Animal feed and feed additives may be used to feed livestock, including but not limited to cattle, hogs, poultry, companion animals, such as cats and dogs, as well as aquatic animals such as fin-fish, shrimp, prawns and lobsters. In this regard, it is noted that the microbial mass obtained in accordance with the present disclosure is particularly rich in protein. When using the methods described in accordance with the present invention, it is possible to obtain microbial biomass wherein the concentration of protein in the waste activated sludge is at least about 50% (w/w), the concentration of crude fat is at least about 6.5% (w/w), the concentration of 60% saturated fatty acids is at least about 4% (w/w), and the concentration of Coenzyme Q10 is at least about 0.004% (w/w), and wherein the concentration of individual amino acids in the waste activated sludge is as set forth in

TABLE 1

| Amino Acid | % of Sample |
| --- | --- |
| Alanine | 3.82%-5.40% |
| Arginine | 2.65%-3.60% |
| Aspartic Acid | 6.20%-6.36% |
| Glutamic Acid | 5.60%-8.04% |
| Glycine | 2.81%-3.99% |
| Histidine | 1.05%-1.46% |
| Isoleucine | 2.60%-3.38% |
| Leucine | 4.16%-5.06% |
| Lysine | 3.15%-4.34% |
| Methionine | 1.40%-1.60% |
| Cysteine | 0.35%-0.55% |
| Phenylalanine | 2.55%-3.29% |
| Proline | 2.75%-2.80% |
| Serine | 2.15%-2.82% |
| Taurine | 0.20%-0.30% |
| Threonine | 3.11%-3.70% |
| Tryptophan | 0.80%-0.98% |
| Tyrosine | 2.70%-2.83% |
| Valine | 3.50%-3.61% |
| Total | 51.55%-64.11% |

Thus the present invention includes a microbial biomass composition comprising at least about 50% (w/w) protein, at least about 6.5% (w/w) of crude fat, at least about 4% (w/w) of 60% saturated fatty acids, and at least about 0.004% (w/w) of Coenzyme Q10, and wherein the concentration of individual amino acids is as set forth in Table 1.

In some embodiments, all or a portion of the microbial biomass produced in accordance herewith may be used to inoculate a wastewater stream and grow additional microbial biomass using a wastewater stream or other growth media to cultivate the bacterial biomass, and using the methodologies described herein or others.

In some embodiments, the present invention provides for the use of the modulated wastewater upon having been used to grow bacterial biomass, to dilute a second wastewater stream.

Accordingly, the present invention further provides a method for growing microbial mass for the production of waste activated sludge comprising:
(a) providing a first aqueous wastewater stream;
(b) determining the concentration of each of the micronutrients aluminum, boron, calcium, cobalt, magnesium, manganese, zinc, and any combination, in the first aqueous wastewater stream;
(c) determining the biological oxygen demand (BOD) normalized dose of each of the micronutrients;
(d) modulating the concentration of at least one micronutrient in the first aqueous wastewater stream to provide a micronutrient-modulated aqueous wastewater stream, whereby the micronutrient-modulated aqueous wastewater stream has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day;
(e) growing microbial biomass using the micronutrient-modulated aqueous wastewater stream; and
(f) diluting a second aqueous wastewater stream with the micronutrient-modulated aqueous wastewater stream obtained after the growing of step (e) to obtain a diluted wastewater stream.

The second wastewater stream (in some embodiments) is effluent obtained from the same manufacturing process as the first wastewater stream and, accordingly, may have the same or similar composition as the first wastewater stream. In such embodiments, the modulated wastewater stream used for the production of bacterial biomass is therefore returned to the headworks, and used to dilute water from the headworks. In some embodiments, the second wastewater stream may be effluent obtained from a different manufacturing process. In order to effect dilution of the second wastewater stream by the micronutrient-modulated aqueous wastewater stream, the two wastewater streams are contacted and mixed in for example a holding tank or vessel or and aeration tank to obtain a diluted wastewater stream. Mixture ratios may vary, and in some embodiments, the ratio of micronutrient-modulated wastewater stream to the second wastewater stream (i.e. the dilution ratio) is about 1:1, 1:2, 1:3, 1:4 or 1:5. The diluted wastewater stream may in turn be used to grow microbial biomass in accordance with the methods of the present disclosure or using any other methodology. The effected dilution may result in the reduction of the concentration of certain compounds present in the second wastewater stream that inhibit the growth of microbial organisms and therefore adversely affect microbial growth. Thus, when the diluted wastewater stream is used to grow microbial mass, a further improved microbial biomass may be obtained, and the contaminant level in the wastewater stream may be reduced.

The present invention further provides methods for enriching the microbial mass with respect to one or more microbial strains using an aqueous waste stream as a growth medium. Accordingly the present invention provides a method for growing a microbial community for the production of microbial biomass comprising the steps of:
(a) identifying an aqueous wastewater stream;
(b) obtaining a microbial community sample comprising a plurality of microbial strains from the wastewater stream;
(c) growing the microbial community under a plurality of growing regimens using the aqueous wastewater stream as a substrate to produce microbial biomass;
(d) determining the proportional representation of a microbial strain, or a cellular constituent produced thereby, capable of producing microbial biomass grown under the plurality of growing regimens;
(e) selecting a growing regimen under which the proportional representation of said microbial strain in the microbial biomass, or the cellular constituent produced thereby, is modulated; and
(f) growing the microbial community using the aqueous wastewater stream as a substrate under the selected growing regimen for the production of microbial biomass.

Referring now to FIG. 1, a flow chart illustrating a method 200 of growing a microbial community to produce microbial mass in accordance with some embodiments of the present invention is shown. The method includes, at 201, identifying an aqueous waste stream. The waste stream may be any waste stream including, as hereinbefore mentioned, waste streams comprising contaminants from food production sources, and waste streams having a BOD in excess of 200 mg/liter. Once the aqueous waste stream has been identified, a water sample is obtained from the waste stream at 205, such sample comprising a native microbial community. Sampling methodologies will be generally known to those skilled in the art but essentially involve collecting the representative influent waste stream water in an appropriate vesicle or container. Upon having obtained the sample it is divided into a plurality of identical or near identical samples, for example 2, 3, 4, 5, 6, 7, 8, 9, 10 or more samples, and each sample is used to grow the natively present microbial community under a different growth conditions, using for example flasks or reactors, typically used for laboratory scale microbial cultivation. FIG. 1, for illustrative purposes, shows generating multiple samples, such as by splitting the sample into three samples at 210, 211 and 212, for example. For each of the three samples a growth condition is then selected and the samples are subjected to such different growth conditions, as exemplified in FIG. 1 at 215, 216 and 217.

The growth conditions that are selected may be any growth conditions, provided however that, in accordance herewith, the aqueous waste stream will be used as the primary growth medium. Growth conditions that may be selected and varied include, for example, the concentration of micronutrients and macronutrients, the pH which may for example be acidic, basic or circum-neutral, and the concentration of dissolved oxygen present in the growth medium, which may be varied between for example about 0.1 ppm and about 5.0 ppm, and more preferably between about 1.0 ppm and 2.0 ppm, by mixing of ambient oxygen into the growth medium. In preferred embodiments, the growth conditions are modulated by altering the micronutrient concentration present in the growth medium, including the concentration of aluminum, boron, cobalt, magnesium, manganese and zinc. In order to modulate the concentration of these micronutrients, the concentrations present in the aqueous waste stream thereof are first determined using methodologies as herein described or any other known methodology, and then their concentrations are adjusted as necessary to vary the growth regimen. In some embodiments, the growth conditions are selected in such a manner that each growth condition varies with respect to the concentration of aluminum, boron, cobalt, magnesium, manganese and zinc, provided however that for each growth condition: (i) the BOD normalized dose of aluminum is selected to be in the range of between about 60 mg/day/lb BOD/day and about 285 mg/day/lb BOD/day; (ii) the BOD normalized dose of boron is selected to be in the range between about 115 mg/day/lb BOD/day and about 300 mg/day/lb BOD/day; (iii) the BOD normalized dose of cobalt is selected to be in the range of between about 50 mg/day/lb BOD/day and about 500 mg/day/lb BOD/day; (iv) the BOD normalized dose of magnesium is selected to at least about 100 mg/day/lb BOD/day; (v) the BOD normalized dose of manganese is selected to be in the range of between about 65 mg/day/lb BOD/day and about 220 mg/day/lb BOD/day; and (vi), and the BOD normalized dose of zinc is selected to be in the range between about 115 mg/day/lb BOD/day and about 275 mg/day/lb BOD/day. Thus, the present disclosure also includes a method for growing a microbial community for the production of waste activated sludge comprising:
(a) providing an aqueous waste stream;
(b) obtaining a microbial community sample comprising a plurality of microbial strains from the aqueous waste stream;
(c) growing the microbial community under a plurality of conditions using the aqueous waste medium as a substrate wherein the BOD normalized dose in the growth medium of (i) aluminum is selected to be in the range of between about 60 mg/day/lb BOD/day and about 285 mg/day/lb BOD/day; (ii) boron is selected to be in the range between about 115 mg/day/lb BOD/day and about 300 mg/day/lb BOD/; (iii) cobalt is selected to be in the range of between about 50 mg/day/lb BOD/day and about 500 mg/day/lb BOD/day; (iv) magnesium is selected to at least 100 mg/day/lb BOD/day; (v) manganese is selected to be in the range of between about 65 mg/day/lb BOD/day and about 220 mg/day/lb BOD/day; and (vi), and zinc is selected to be in the range between about 115 mg/day/lb BOD/day and about 275 mg/day/lb BOD/day;
(d) determining the proportional representation of a microbial strain, or a desirable constituent thereof, capable of producing microbial biomass grown under the plurality of growing regimens;
(e) selecting a growing regimen under which the proportional representation of said microbial strain in the microbial biomass, or a cellular constituent produced thereby, is modulated; and
(f) growing the microbial community using the aqueous waste stream as a substrate under the selected growing regimen for the production of microbial biomass.

Growth times may vary and may take several days. In general, growth will be continued until a certain cell density is obtained, which may for example be one to three mean cell residence times. Normal MCRTs that are applicable to this process range from 4-10 days and it is therefore common to require at least 4, and up to 30, days to achieve a stable cell density. Upon having achieved a desirable density a biological analysis of each of the samples is performed by measuring the proportional representation of one or more microbial strains or a constituent produced thereby in each of the three samples collected at 220, 221 and 222. This may include a quantitative analysis using direct cell counting techniques, including the use of microscopy, polynucleotide quantification, protein content, phospholipid fatty acid analysis, quantitative PCR protein analysis etc. The identification of the genera and/or species of one or more of the members in the microbial community may also be conducted. For example, an analysis of the DNA of the microorganisms may be performed, where DNA is optionally cloned into a vector and a suitable host cell to amplify the DNA and facilitate detection. In some embodiments, all or part of the ribosomal RNA (rRNA) may be used for identification purposes.

Detection may be by use of any appropriate means known to a person of skill in the art. Non limiting examples include restriction fragment length polymorphism (RFLP); terminal restriction fragment length polymorphism (TRFLP); polymerase chain reaction (PCR); DNA-DNA hybridization, such as with a probe, Southern analysis, or the use of an array, microchip, bead array; denaturing gradient gel electrophoresis; and DNA sequencing. In some embodiments, the microbial strain of which the proportional representation is modulated in 220, 221 and 222 is a microbial strain capable of producing a desirable cellular compound, such as protein, crude fat, saturated fatty acid, Coenzyme Q10 or an amino acid. Thus desirable constituents that may be detected and measured under each of the various growth conditions include protein, crude fat, saturated fatty acid, Coenzyme Q10 or an amino acid. Alternatively, certain toxic compounds may be detected and measured. The growth condition under which the concentration of the selected microorganism or desirable constituent is most desirable is identified at 225. It is noted that in certain instances high concentrations of such microorganisms or desirable constituents are desirable, for example high concentrations of protein, crude fat, saturated fatty acid, Coenzyme Q10 or an amino acid, and in other instances low concentrations may be desirable, for example a toxic compound or other compound that inhibits the production of microbial biomass. The selected growth condition is then applied to bulk growth of the microbial community for the production of waste active sludge at 230.

The present disclosure is further described by reference to the following illustrative, non-limiting examples.

EXAMPLES

Micronutrient Modulation of an Aqueous Wastewater Stream from a Brewery

Figure 2:
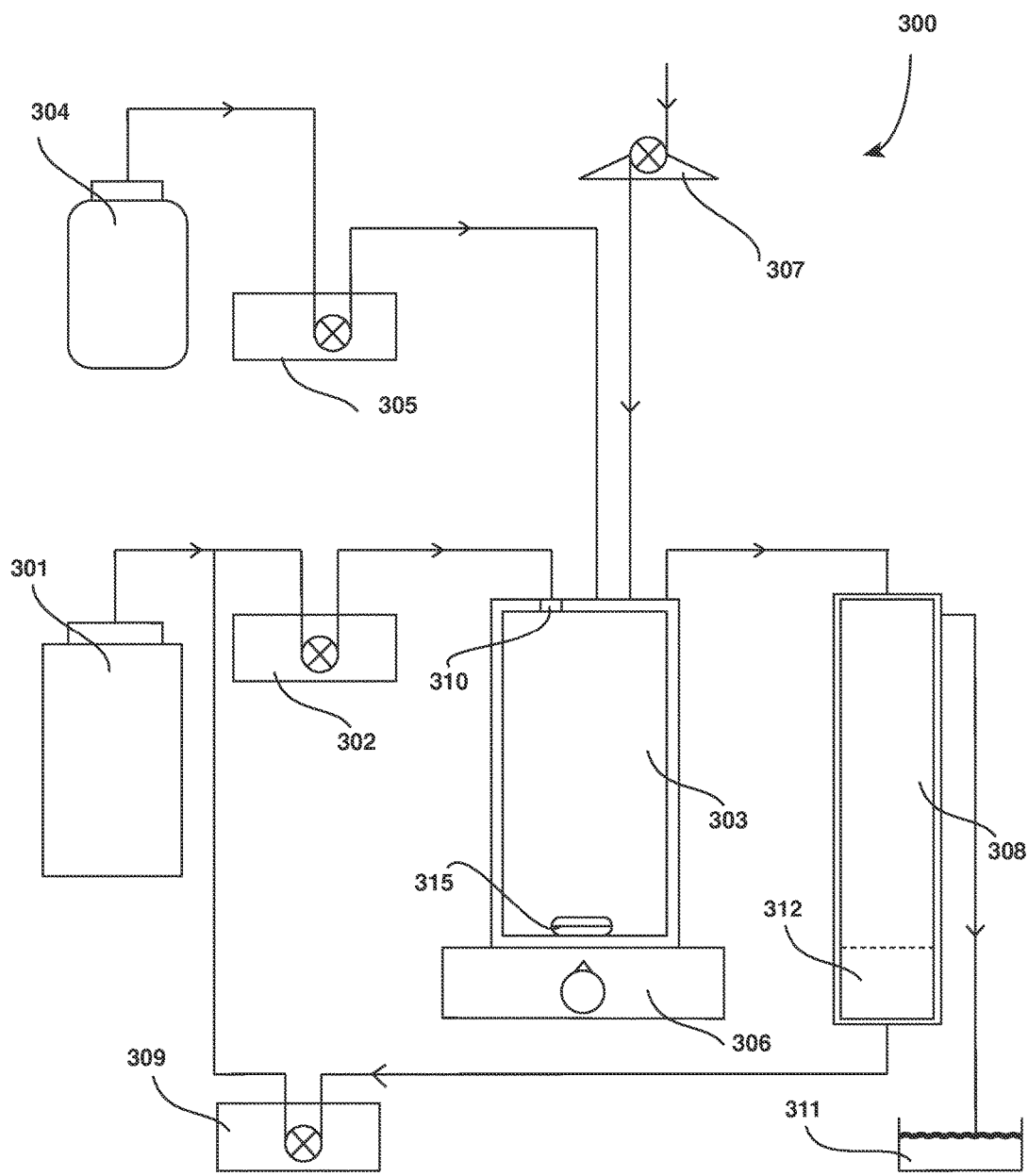
FIG. 2. depicts a schematic of a laboratory-scale reactor used to treat wastewater and produce microbial biomass under a plurality of conditions, in accordance with some embodiments.

A sample of wastewater was collected from the effluent from a large brewery. The sample was delivered to the lab where the biological oxygen demand was measured using the Standard Method (Standard Methods for the Examination of Water and Wastewater, $22^{nd}$ edition, E. U. Rice et. al, editors. 2012. *American Public Health Association, American Water Works Association, Water Environment Federation*, publishers. Washington, D.C. USA) and metals concentrations were determined using inductively coupled plasma spectroscopy (ICP). In the laboratory, three small-scale wastewater treatment reactors were assembled. Referring to FIG. 2, there is shown a schematic of the small-scale reactor for wastewater treatment operation (300). Nitrogen (in the form of urea) and phosphorus (in the form phosphoric acid) were added to the wastewater sample (301) in order to achieve BOD:N:P ratios of 100:10:1 so that these macronutrients would not limit microbial growth. The wastewater was then pumped continuously using a pump (302) into a constantly stirred reactor (303). Simultaneously, the micronutrients aluminum, boron, cobalt, manganese, and zinc were added from a reservoir (304) in varying concentrations and ratios, to the influent wastewater of the reactors receiving an additional dose of micronutrients and according to Table 2 below. The third reactor was designated a control reactor and was not amended with micronutrients beyond what was present in the wastewater collected at the brewery. The influent wastewater was continuously supplied to all three reactors using a pump (305) following measurement of the concentration of each of these micronutrients in the sample to achieve concentrations of micronutrients within the herein prescribed concentration ranges. It is noted that no magnesium was added because its concentration in the wastewater already exceeded 100 mg/day/lb BOD/day.

Stirring of the growth medium reactor was achieved via a magnetic stir plate (306) and a stir bar (315) and air was added via an aquarium pump (307) to achieve targeted dissolved oxygen between 1.0 ppm and 5.0 ppm. Reactors (1 L, 303) were initially amended with the bacteria-containing RAS, WAS, or MLSS from the WWTP in an amount consistent with the food:microorganism ratio implemented at the plant from which they were collected. The continuously pumped wastewater influent was allowed to enter the reactor vessel and reside approximately 0.25 days in this vessel (i.e. the hydraulic residence time or HRT was 0.25 days) and then allowed to overflow together with the cells continuously to a clarifier (308). Cells within the clarifier settled to the bottom (312) where they were returned to the reactor via a pump (309) and re-enter the aerated reactor at the influx point (310) together with the influent wastewater (301). Clean water was then allowed to overflow from the clarifier to the drain (311). The reactors were then run continuously for two to three MCRTs to achieve equilibrium. During this time, the mean cell residence time (MCRT) was controlled by wasting cells to achieve the targeted age; generally, about 7 days. Wasted cells were dried in a freeze dryer and protein was measured using a Leco FP628 protein analyzer.

The concentrations of each of the micronutrients in the wastewater stream pre- and post-modulation of the concentration of micronutrients are shown in Table 2.

TABLE 2

Concentration of micronutrients in brewery wastewater using the reactor system and conditions described in Example 1, before and after modulation of the concentration of micronutrients.

|  | Reactor 1 | Reactor 2 | Reactor 3 (Control) |
| --- | --- | --- | --- |
| PRE MODULATION | | | |
| Al mg/d/lb BOD/d | <11.4 | <11.4 | <11.4 |
| B mg/d/lb BOD/d | 30.2 | 30.2 | 30.2 |
| Co mg/d/lb BOD/d | 11.2 | 11.2 | 11.2 |
| Mg mg/d/lb BOD/d | >100 | >100 | >100 |
| Mn mg/d/lb BOD/d | 52.5 | 52.5 | 52.5 |
| Zn mg/d/lb BOD/d | 19.7 | 19.7 | 19.7 |
| POST MODULATION | | | |
| Al mg/d/lb BOD/d | 65.7 | 65.7 | <11.4 |
| B mg/d/lb BOD/d | 262.7 | 262.7 | 30.2 |
| Co mg/d/lb BOD/d | 197.0 | 197.0 | 11.2 |
| Mg mg/d/lb BOD/d | >100 | >100 | >100 |
| Mn mg/d/lb BOD/d | 72.2 | 72.2 | 52.5 |
| Zn mg/d/lb BOD/d | 131.3 | 131.3 | 19.7 |

2. Supplying Micronutrients

As Example 1, where the micronutrients are first dissolved in water or another solvent such as citric acid, and then pumped to the small-scale reactor to achieve targeted levels.

3. Supplying Micronutrients

As Example 1, where the micronutrients are fed into the influent wastewater, the RAS, or both simultaneously in powder form, preferably through the use of a conveyor or auger.

4. Supplying Micronutrients

As Example 1, where any of the micronutrient concentrations, or any combinations of the micronutrients shown in Tables A-F, are achieved by adding Al, B, Co, Mn, Mg, and Zn as needed and either in liquid or powder form.

5. Obtaining Microbial Cells

As Example 1, where the cells are obtained from the reactor system, centrifuged to form a pellet and then dried.

6. Obtaining Microbial Cells

As Example 1, where the cells are allowed to settle in order to thicken by gravity or are concentrated by pressing prior to drying.

7. Obtaining Microbial Cells

As Example 1, where the wasted cells are dried in a lab tray dryer, a rotary dryer, a ring dryer, a flash dryer, or other suitable dryer that does not alter protein content.

8. Determination of Protein Concentration

As Example 1, where crude protein content is measured by total kjeldahl nitrogen (TKN) or digestion of the produced biomass and measurement of total nitrogen. Crude protein is then extrapolated from total nitrogen or TKN using a correction factor.

9. Measurement of SSV and Reduction of SSV in Micronutrient Modulated Reactor

As Example 1, where the approximate filamentous microorganism concentration at Time=0 is measured microscopically and SSV at Time=0 is measured using a settleometer. A micronutrient combination and concentration is then added using Tables A-F as the limit for upper and lower concentrations and for possible combinations. After one to three MCRTs, the filamentous microorganism concentration and SSV are measured again. An increase in filament concentration or SSV would lead to an alteration of the concentrations and/or combinations of micronutrients supplied to the small-scale reactor. At the point where the new micronutrient concentration and/or micronutrient combination was delivered to the small-scale reactor, the experimental time is reset to Time=0. A decrease or lack of change in SSV and filament concentration at one MCRT would then lead to a continuation of the experiment to two and three MCRTs. If the reduction in SSV and filament concentration continues, then the reactor will be allowed to equilibrate past three MCRTs and protein content of the wasted cells will be measured. Optimized micronutrient concentrations can then be determined using filament concentration, SSV, and protein content as the response variables. Actual settleometer and SVI data are provided below.

In this example, a fraction of the influent wastewater at a large-scale brewery was directed to a reactor as described in Example 1 with the exception that the aerobic basin was 175 L of volume. The influent was then modulated with nitrogen, phosphorus, and micronutrients as described in Example 1 and a settling test was conducted after 2 MCRTs (in this case, 14 days). The results are shown below in Table 3.

TABLE 3

SSV Measurements of non-modulated and micronutrient modulated wastewater

| Time (min) | Full-scale MLSS (not macro- or micronutrient modulated) (volume in ml) | Reactor-scale (macro- and micronutrient modulated) (volume in ml) |
| --- | --- | --- |
| 0 | 1000 | 1000 |
| 5 | 960 | 550 |
| 10 | 945 | 445 |
| 15 | 915 | 380 |
| 20 | 880 | 340 |
| 25 | 790 | 315 |
| 30 | 720 | 290 |
| 60 | 520 | 240 |
| 120 | 365 | 230 |
| 180 | 295 | 220 |
| SVI ml/g | 171 | 95 |

The data in Table 3 above shows a reduction in the SSV in the micronutrient modulated wastewater stream.

10. Reduction of SSV

As Example 9, where the concentration and combination of micronutrients required to reduce filament concentration and SSV is determined and delivered to the small-scale reactors until filament concentrations are negligible as measured by SSV. At that point, the ratio of the micronutrient addition is maintained but the feed rate and therefore, the resulting concentration within the small-scale reactor, are reduced until an increase in filament concentration and SSV is observed. The micronutrient feed rate is then maintained at a level slightly above that at which the increase in filamentous microorganisms and SSV was observed.

11. Microbial Mass Production and Protein Content Measurement Under a Plurality of Micronutrient Growth Conditions.

Four reactor set ups as described in Example 1 were assembled and operated for a period of 2 weeks each. The micronutrient concentrations in the reactors were varied as specified in Table 4 with two of the reactors (Reactor 1 and Reactor 2) receiving micronutrient and macronutrient modulated wastewater and two that did not (labeled the "Controls"). The BOD:N:P ratio was adjusted to 100:10:1 as in Example 1 in all four reactors. During this period, the filamentous microorganism concentration and the SSV were measured as in example 9. Samples were also taken from the aerated reactors or the clarifiers, centrifuged to a pellet and dried in a freeze dryer or a thermal dryer at a relatively low temperature (approximately 65° C.). Protein was then analyzed using a Leco FP 628 protein analyzer. The results are shown in Table 4:

TABLE 4

Protein concentrations measured in microbial mass supplied with different micronutrient concentrations:

| | Reactor 1 | Reactor 2 | Reactor 3 Control[b] | Reactor 4 Control[b] |
| --- | --- | --- | --- | --- |
| Al mg/d/lb BOD/d | 65.7 | 124.3 | <11.4 | 59.1 |
| B mg/d/lb BOD/d | 262.7 | 124.3 | 30.2 | 49.1 |
| Co mg/d/lb BOD/d | 197.0 | 62.2 | 11.2 | 13.7 |
| Mg mg/d/lb BOD/d | >100 | >100 | >100 | >100 |
| Mn mg/d/lb BOD/d | 72.2 | 124.3 | 52.5 | 69.0 |
| Zn mg/d/lb BOD/d | 131.3 | 248.6 | 19.7 | 25.5 |
| Crude Protein % | 65.9% | 62.5% | Not measurable[a] | 47% |

[a]this reactor grew a concentration of filamentous organisms that resulted in the washing out of the reactor and the loss of solids from the aerobic basin.
[b]control reactors were not amended with micronutrients. The values shown in Table 4 represent the concentration found in the wastewater produced by the brewery.

The highest concentration of protein was then used to determine the optimal micronutrient concentrations where good settling characteristics were observed; for example, where filamentous microorganisms were "rare" in Table 4, reactor 1 provided the best results of these metrics.

12. Micronutrient Modulation of an Aqueous Wastewater Stream from a Brewery—Effect on Growth of Filamentous Microorganisms.

Using the same experimental laboratory-scale reactor as Example 1, three reactors were established that utilize identical brewery wastewater as a growth substrate. The wastewater influent was amended with nitrogen and phosphorus as in Example 1 to achieve a BOD:N:P ratio of 100:10:1. Two of the reactors (Reactor 1 and Reactor 2) were then amended with micronutrients as explained in Example 1 and one was not (Reactor 3). The concentration of micronutrients in Reactor 3 is indicative of the micronutrient concentration found in the wastewater before amendment. The growth of filamentous microorganisms was monitored and measured as summarized in Table 5.

TABLE 5

Growth of filamentous microorganisms

| | Reactor 1 modulated | Reactor 2 modulated | Reactor 3 non-modulated |
|---|---|---|---|
| Al mg/d/lb BOD/d | 65.7 | 124.3 | <11.4 |
| B mg/d/lb BOD/d | 262.7 | 124.3 | 30.2 |
| Co mg/d/lb BOD/d | 197.0 | 62.2 | 11.2 |
| Mg mg/d/lb BOD/d | >100 | >100 | >100 |
| Mn mg/d/lb BOD/d | 72.2 | 124.3 | 52.5 |
| Zn mg/d/lb BOD/d | 131.3 | 248.6 | 19.7 |
| Filamentous Organism - visual observations[a] | "Rare" | "Rare" | "Excessive" |
| SVI ml/g | 135 | 140 | 690 |

[a]Marshall, Rick and Mike Richard, 2010. Activated Sludge Microbiology Poster. METC Group. Corvallis, OR USA.

Over time, the relative numbers of filamentous bacteria were quantified as well as relative settleability, and total suspended solids in the effluent from the reactors. The results showed a decreasing concentration of filamentous bacteria in the reactors that received the micronutrient mixture together with lower effluent total suspended solids and as observed by better settling within the clarifier. Over a period of approximately one to two weeks, the reactors receiving the micronutrients developed a stable MLSS concentration with good settleability in the clarifier and effluent solids concentrations less than 20 ppm.

As observed with a microscope at 400×-1000× magnification, the relative concentration of filamentous bacteria steadily decreased during this period and the effluent TSS was consistently below 30 mg/L. In contrast, the relative concentration of filaments in the reactor not amended with micronutrients increased over time and this increase was accompanied by poor settling in the clarifier and very high concentrations of solids in the effluent (100 ppm to 600 ppm). Over the same period, the elution of solids from the clarifier in the effluent resulted in the "washing out" of the reactor, i.e. a steadily declining MLSS concentration as a result of solids being lost in the effluent and their not being returned to the reactor in the RAS flow was observed.

13. SSV Measurements

As Example 12, where the micronutrient concentrations and/or combinations were altered after one to three MCRTs due to the fact that filamentous microorganism concentration did not decrease, SSV did not decrease or was not adequate to achieve effluent suspended solids within targeted ranges, and/or protein content of the produced biomass was not in excess of 50% or within the targeted range.

14. Diluting of a Wastewater Stream with a Macronutrient-Modulated Wastewater Stream Using the same experimental laboratory scale wastewater plant setup as in Example 1, a sample of palm oil mill wastewater was split into three portions. N and P were added to achieve a BOD:N:P ratio of 100:10:1 but micronutrients were not added because their concentration in the palm oil mill wastewater is in excess of the levels described above. The pH was adjusted to slightly alkaline with NaOH (sodium hydroxide) and was maintained between 7 and 8 for the duration of the experiment with same. Referring to FIG. 2 the treated effluent (311) was plumbed so that a percentage of it was returned to the point of entry into the reactors (310). The flow rate was adjusted so that the influent was diluted with treated effluent at ratios of 1:1 up to 1:4, on a volume basis. The pH was not adjusted in the sample that was diluted 1:6. Protein concentrations were measured using the same methodologies use in Example 1. The results are shown in Table 6 below.

TABLE 6

Protein concentrations measured in microbial mass recovered from a waste stream diluted with a macronutrient-modulated wastewater stream

| Experiment # | 1 | 2 | 3 | 4 | 5 |
|---|---|---|---|---|---|
| pH circumneutral | Yes | Yes | Yes | No | Yes |
| Dilution | 1:1 | 1:2 | 1:3 | 1:4 | 1:4 |
| Protein Content | 55% | 61% | 65% | 27% | 58% |

15. Modulation of Aluminum in Brewery Wastewater Stream

A reactor set up as described in Example 1 may be assembled. Macronutrient concentrations may be adjusted as described in Example 1. Micronutrient concentrations in the growth medium in the reactor 303 may be measured and subsequently modulated in accordance with any of the micronutrient concentration combinations set forth in Table A, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

16. Modulation of Boron in Brewery Wastewater Stream

A reactor set up as described in Example 1 may be assembled. Macronutrient concentrations may be adjusted as described in Example 1. Micronutrient concentrations in the growth medium in the reactor 303 may be measured and subsequently modulated in accordance with any of the micronutrient concentration combinations set forth in Table B, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

17. Modulation of Cobalt in Brewery Wastewater Stream

A reactor set up as described in Example 1 may be assembled. Macronutrient concentrations may be adjusted as described in Example 1. Micronutrient concentrations in the growth medium in the reactor 303 may be measured and subsequently modulated in accordance with any of the micronutrient concentration combinations set forth in Table C, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

18. Modulation of Magnesium in Brewery Wastewater Stream

A reactor set up as described in Example 1 may be assembled. Macronutrient concentrations may be adjusted as described in Example 1. Micronutrient concentrations in the growth medium in the reactor 303 may be measured and subsequently modulated in accordance with any of the micronutrient concentration combinations set forth in Table D, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

19. Modulation of Manganese in Brewery Wastewater Stream

A reactor set up as described in Example 1 may be assembled. Macronutrient concentrations may be adjusted as described in Example 1. Micronutrient concentrations in the growth medium in the reactor 303 may be measured and subsequently modulated in accordance with any of the micronutrient concentration combinations set forth in Table E, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

20. Modulation of Zinc in Brewery Wastewater Stream

A reactor set up as described in Example 1 may be assembled. Macronutrient concentrations may be adjusted as described in Example 1. Micronutrient concentrations in the growth medium in the reactor 303 may be measured and subsequently modulated in accordance with any of the micronutrient concentration combinations set forth in Table F, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

21. Micronutrient Modulation of an Aqueous Wastewater Stream from a Wet Corn Miller.

A sample of wastewater was collected from the effluent from a large facility involved with the wet milling of corn. The sample was delivered to the lab where the biological oxygen demand was measured using the Standard Method (Standard Methods for the Examination of Water and Wastewater, 22$^{nd}$ edition, E. U. Rice et. al, editors. 2012. *American Public Health Association, American Water Works Association, Water Environment Federation*, publishers. Washington, D.C. USA) and metals concentrations were determined using inductively coupled plasma spectroscopy (ICP). In the laboratory, a small-scale wastewater treatment operation was assembled. Referring to FIG. 2, there is shown a schematic of the small-scale reactor for wastewater treatment operation (300). Nitrogen (in the form of urea) and phosphorus (in the form phosphoric acid) were added to the wastewater sample (301) in order to achieve BOD:N:P ratios of 100:10:1 so that these macronutrients would not limit microbial growth. The wastewater was then pumped continuously using a pump (302) into a constantly stirred reactor (303). Simultaneously, the micronutrients aluminum, boron, cobalt, manganese, and zinc were added from a reservoir (304) in varying concentrations and ratios, to the influent wastewater continuously supplied using a pump (305) following measurement of the concentration of each of these micronutrients in the sample.

Stirring of the growth medium reactor was achieved via a magnetic stir plate (306) and a stir bar (307) and air was added via an aquarium pump (307) to achieve targeted dissolved oxygen between 1.0 ppm and 5.0 ppm. Reactors (1 L, 303) were initially amended with the bacteria-containing RAS, WAS, or MLSS from the WWTP in an amount consistent with the food:microorganism ratio implemented at the plant from which they were collected. The continuously pumped wastewater influent was allowed to enter the reactor vessel and reside approximately 0.25 days in this vessel (i.e. the hydraulic residence time or HRT was 0.25 days) and then allowed to overflow together with the cells continuously to a clarifier (308). Cells within the clarifier settled to the bottom (312) where they were returned to the reactor via a pump (309) and re-enter the aerated reactor at the influx point (310) together with the influent wastewater (301). Clean water was then allowed to overflow from the clarifier to the drain (311). The reactors were then run continuously for two to three MCRTs to achieve equilibrium. During this time, the mean cell residence time (MCRT) was controlled by wasting cells to achieve the targeted age; generally, about 7 days. Wasted cells were dried in a freeze dryer and protein was measured using a Leco FP628 protein analyzer.

22. Modulation of Aluminum in Corn Mill Wastewater Stream

A reactor set up as described in Example 21 may be assembled. Macronutrient concentrations may be adjusted as described in Example 21. Micronutrient concentrations in the growth medium in the reactor 303 may be measured and subsequently modulated in accordance with any of the micronutrient concentration combinations set forth in Table A, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

23. Modulation of Boron in Corn Mill Wastewater Stream

A reactor set up as described in Example 21 may be assembled. Macronutrient concentrations may be adjusted as described in Example 21. Micronutrient concentrations in the growth medium in the reactor 303 may be measured and subsequently modulated in accordance with any of the micronutrient concentration combinations set forth in Table B, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

24. Modulation of Cobalt in Corn Mill Wastewater Stream

A reactor set up as described in Example 21 may be assembled. Macronutrient concentrations may be adjusted as described in Example 21. Micronutrient concentrations in the growth medium in the reactor 303 may be measured and subsequently modulated in accordance with any of the micronutrient concentration combinations set forth in Table C, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

25. Modulation of Magnesium in Corn Mill Wastewater Stream

A reactor set up as described in Example 21 may be assembled. Macronutrient concentrations may be adjusted as described in Example 21. Micronutrient concentrations in the growth medium in the reactor 303 may be measured and subsequently modulated in accordance with any of the micronutrient concentration combinations set forth in Table D, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

26. Modulation of Manganese in Corn Mill Wastewater Stream

A reactor set up as described in Example 21 may be assembled. Macronutrient concentrations may be adjusted as described in Example 21. Micronutrient concentrations in the growth medium in the reactor 303 may be measured and subsequently modulated in accordance with any of the micronutrient concentration combinations set forth in Table E, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

27. Modulation of Zinc in Corn Mill Wastewater Stream

A reactor set up as described in Example 21 may be assembled. Macronutrient concentrations may be adjusted as described in Example 21. Micronutrient concentrations in the growth medium in the reactor 303 may be measured and subsequently modulated in accordance with any of the micronutrient concentration combinations set forth in Table F, by adjusting the micronutrient concentrations in reservoir 304. Following microbial growth for a period of 2 weeks, protein concentration of the microbial mass 312 obtained from the clarifier 308 may be measured as described in Example 2, and the presence of filamentous microorganisms in the microbial mass may be determined as set forth in Example 9.

28. Modulation of Micronutrients in Rice Mill Wastewater Stream

A sample of wastewater may be collected from the effluent from a large wet rice miller or parboiler. A reactor setup may be assembled and operated as in Examples 21-27.

29. Modulation of Micronutrients in Citrate Wastewater Stream

A sample of wastewater may be collected from the effluent from a large citrate producer. A reactor setup may be assembled and operated as in Examples 21-27.

30. Modulation of Micronutrients in Beet- or Sugar-Cane Wastewater Stream

A sample of wastewater may be collected from the effluent from a beet- or cane-sugar manufacturer. A reactor setup may be assembled and operated as in Examples 21-27.

31. Modulation of Micronutrients in Potato-Processing Wastewater Stream

A sample of wastewater may be collected from the effluent from a large potato processor. A reactor setup may be assembled and operated as in Examples 21-27.

32. Modulation of Micronutrients in Alcohol Distilling Wastewater Stream

A sample of wastewater may be collected from the effluent from a large alcohol distiller. A reactor setup may be assembled and operated as in Examples 21-27.

33. Modulation of Micronutrients in Fruit Processing Wastewater Stream

A sample of wastewater may be collected from the effluent from a large fruit processor or juice manufacturer. A reactor setup may be assembled and operated as in Examples 21-27.

34. Modulation of Micronutrients in Starch Processing Wastewater Stream

A sample of wastewater may be collected from the effluent from a large food starch manufacturer. A reactor setup may be assembled and operated as in Examples 21-27.

35. Modulation of Micronutrients in Dairy Processing Wastewater Stream

A sample of wastewater may be collected from the effluent from a large dairy processor. A reactor setup may be assembled and operated as in Examples 21-27.

36. Modulation of Micronutrients in Fruit or Vegetable Processing Wastewater Stream Comprising Organic Nutrients A sample of wastewater may be collected from the effluent from a large processor of fruit- or vegetable-derived products that results in carbohydrates, fats, or proteins being entrained in the wastewater. A reactor setup may be assembled and operated as in Examples 21-27.

37. Modulation of Micronutrients Animal Derived Products Processing Wastewater Stream Comprising Organic Nutrients A sample of wastewater may be collected from the effluent from a large processor of animal-derived products that results in carbohydrates, fats, or proteins being entrained in the wastewater. A reactor setup may be assembled and operated as in Examples 21-27.

38. Modulation of Micronutrients in Wastewater Stream Comprising Organic Nutrients Obtained from Animal Rendering or Slaughtering Facility A sample of wastewater may be collected from the effluent from a large animal slaughtering or animal rendering operation that results in carbohydrates or proteins being entrained in the wastewater. A reactor setup may be assembled and operated as in Examples 21-27.

39. Micronutrient Modulation of Wastewater from Full-Scale Facilities

Data regarding micronutrient combinations, micronutrient concentrations, and MCRT may be applied to a full-scale wastewater treatment plant serving a brewery, alcohol distiller, citrate producer, fruit juicer or processor, dairy processor, potato processor, starch manufacturer, wet rice miller or parboiler, beet- or cane-sugar manufacturer, fruit or vegetable derived products manufacturer, animal-derived products manufacturer, slaughtering operation, or rendering operation.

The operating regimen from a reactor utilizing the identical wastewater substrate and demonstrating good performance in the form of high protein content in the biomass is transferred to the full-scale. The dissolved oxygen level in the aerobic basin is set to 2.0 mg/l. Nitrogen is added to the influent wastewater via a storage vessel and pump and/or solids conveyor and in the form of urea, ammonia, ammonium nitrate, manure, or other forms in order to achieve a BOD:N ratio of 100:10. In some instances, nitrogen content of the wastewater may be adequate so that further addition is not required. Simultaneously, phosphorus is added using a storage vessel and pump and in the form of phosphoric acid or a dissolved phosphate salt to achieve a BOD:P ratio of 100:1. In some instances, phosphorus content of the wastewater may be adequate so that further addition is not required. Next, the plumbing is modified so that the return activated sludge (RAS) is pumped into a pipe, tank, or other vessel containing the influent wastewater prior to introduction into the aerobic basin. Next, micronutrients are prepared using the concentrations and combinations determined at the reactor-scale. The micronutrient mixture is blended in a manner that results in a highly concentrated solution while maintaining the pre-determined concentration ratios between micronutrients. A dry micronutrient blend can then be delivered to the influent wastewater using an auger or solids conveyor. Alternatively, dry micronutrients may be added to a tank containing a solvent such as water, citric acid, or other suitable liquid carrier and mixed to dissolve. A pump is then used to deliver the micronutrients into the influent wastewater, the RAS stream, or into the vessel where the RAS contact the influent wastewater and prior to any of three components' being introduced into the aerobic basin.

The MCRT of the wastewater treatment plant is then reduced to a value below 10 days, and ideally to 6 or 7 days, by wasting ample quantities of biomass from the system to reduce the MCRT by one day per day. Settleability of the biomass in the wastewater treatment plant is monitored using a settleometer, by coring a gravity clarifier, and/or by measuring effluent suspended solids. The reduction in MCRT to approximately 10, 9, 8, 7, 6 days or lower continues until settleability problems exhibit. At that point, the MCRT reduction ceases and settleability continues to be monitored. If settleability equilibrates at an acceptable level, MCRT is maintained. If not, MCRT is increased by approximately one day per week until acceptable settleability is achieved as measured using a settleometer, by coring a gravity clarifier, or, most importantly, by measuring the treated effluent suspended solids and ensuring that they are within permitted levels.

During the process of lowering MCRT, treated effluent concentrations of ammonia, nitrate, total nitrogen and phosphorus are monitored. The delivery rates of these nutrients are altered so that a very small residual is present in the treated effluent that is below effluent permit levels. As necessary, their delivery into the influent wastewater is increased or decreased to achieve these targeted levels.

The process is then allowed to equilibrate for a period of two to three MCRTs. During this period, samples of MLSS or RAS are collected, centrifuged, dried, and analyzed for protein content.

40. Micronutrient Addition to Wastewater from Full-Scale Facilities

As Example 39 where the micronutrients are purchased in liquid form, blended in a tank, and delivered to the influent wastewater and/or RAS using a pump.

41. Micronutrient Addition to Wastewater from Full-Scale Facilities

As Example 39, where the pipe or tank where the influent wastewater, the nutrients, and the RAS is sized to allow at least 30 minutes of contact time and without aeration.

42. Micronutrient Addition to Wastewater from Full-Scale Facilities

As Example 39, where the pipe or tank where the influent wastewater, the nutrients, and the RAS contact is sized to allow at least 30 minutes of contact time and with aeration.

43. Modulation of the Concentration Al, B, Co, Mg, Mn and/or Zn of Wastewater from Full-Scale Facilities As Example 39, where the micronutrient amendments include any combination and concentration possibility shown in Tables A-F.

44. Dilution of Wastewater Stream to Modulate Micronutrient Concentration

As Example 39, where a portion of the treated effluent is pumped back to the headworks of the plant such that the influent wastewater is diluted with the treated effluent.

45. Monitoring of Filamentous Microorganisms of Wastewater from Full-Scale Facilities As Example 39, where filamentous microorganism concentration is monitored using microscopy techniques. The micronutrient dose is increased higher until a reduction of filament concentration is observed. The micronutrient concentration is then reduced by 10% per week while observing filamentous microorganism concentrations. This reduction in micronutrient concentration continues until an increase in filament concentration occurs. The micronutrient dose is then held constant while observing the filament concentration. If it stays constant, the micronutrient dose is not changed. If it increases, the micronutrient dose is increased by 10% or until the filament concentration is stabilized.

46. Monitoring of Filamentous Microorganisms of Wastewater from Full-Scale Facilities As Example 45, where the micronutrient dose is increased for a second time and until a significant reduction in filaments occurs. The micronutrient dose is then reduced by 10% per week until the concentration is obtained above which the increase in filaments was observed in Example 45. The micronutrient dose is then held constant at this level.

47. Removal of Al, B, Co, Mg, Mn and/or Zn from Full-Scale Facilities

As Example 1 where all or part of the initial wastewater is treated with ion exchange, precipitation methodology, or other means to remove one or more micronutrients present in the wastewater prior to its being amended with micronutrients as specified in Tables A-F. This removal may be complete or partial, depending on the desired final concentration of the micronutrient or micronutrients being removed.

48. Micronutrient Modulation of the Full-Scale Aqueous Wastewater Stream from a Brewery.

A large brewer of beer with a dedicated aerobic, biological wastewater treatment plant was located. Metals concentrations from the effluent from the brewery were determined using inductively coupled plasma spectroscopy (ICP). The historical biological oxygen demand in the wastewater was determined from plant records, if possible. Otherwise, BOD levels were determined using the Standard Method (Standard Methods for the Examination of Water and Wastewater, 22$^{nd}$ edition, E. U. Rice et. al, editors. 2012. *American Public Health Association, American Water Works Association, Water Environment Federation*, publishers. Washington, D.C. USA). A chemical delivery system was constructed so that nitrogen, phosphorus, and micronutrients could be added to the influent wastewater stream to achieve a BOD:N:P ratio of 100:10:1 and concentrations of micronutrients as shown in Tables A-F in the aerobic basin. Dissolved oxygen levels in the aerobic basin were maintained at 1.5-2.5 mg/L by adjusting the rate of flow from the blowers, compressors, or other type of air delivery devices present at the wastewater treatment facility. The mean cell residence time (MCRT) was controlled by wasting cells from the wastewater treatment plant to achieve the lowest MCRT where the settling characteristics allow for the meeting of permitted or targeted total suspended solids levels in the effluent. The resulting biosolids mass are then used as an animal feed ingredient.

49. Modulation of MCRT of Wastewater Obtained from Brewery

As Example 48, where the MCRT is maintained at less than 10 days.

50. Modulation of MCRT of Wastewater Obtained from Brewery

As Example 48, where the MCRT is maintained at 9 days.

51. Modulation of MCRT of Wastewater Obtained from Brewery

As Example 48, where the MCRT is maintained at 8 days.

52. Modulation of MCRT of Wastewater Obtained from Brewery

As Example 48, where the MCRT is maintained at 7 days.

53. Modulation of MCRT of Wastewater Obtained from Brewery

As Example 48, where the MCRT is maintained at 6 days.

54. Modulation of MCRT of Wastewater Obtained from Brewery

As Example 48, where the MCRT is maintained at 5 days.

55. Modulation of MCRT of Wastewater Obtained from Brewery

As Example 48, where the MCRT is maintained at 4 days.

56. Modulation of MCRT of Wastewater Obtained from Brewery

As Example 48, where the MCRT is maintained at less than 4 days.

57. Addition of Nitrogen to Wastewater Obtained from Brewery

As Example 48, where the added nitrogen is in the form of urea.

58. Addition of Nitrogen to Wastewater Obtained from Brewery

As Example 48, where the added nitrogen is in the form of ammonium nitrate.

59. Addition of Nitrogen to Wastewater Obtained from Brewery

As Example 48, where the added nitrogen is in the form of anhydrous ammonia.

60. Addition of Nitrogen to Wastewater Obtained from Brewery

As Example 48, where the added nitrogen is in the form of animal manure.

61. Addition of Phosphorus to Wastewater Obtained from Brewery

As Example 48, where the added phosphorus is in the form of phosphoric acid.

62. Addition of Phosphorus and Nitrogen to Wastewater from Brewery

As Example 48, where the return activated sludge is plumbed to a location where it contacts the influent wastewater and the amended nitrogen, phosphorus, and micronutrients simultaneously.

63. Addition of Phosphorus and Nitrogen to Wastewater from Brewery

As Example 62, where this location is a tank, pipe, or other vessel where a contact time of 2-20 minutes can be maintained.

64. Addition of Micronutrients and Macronutrients to Wastewater from Brewery

As example 48, where the micronutrients, nitrogen, and phosphorus are plumbed to be added directly to the aerobic basin(s).

65. Addition of Nitrogen to Wastewater from Brewery

As Example 48, where the nitrogen is added at a rate to achieve a BOD:N ratio of 100:6-20.

66. Addition of Phosphorus to Wastewater from Brewery

As Example 48, where phosphorus is added to achieve a BOD:P ratio of 100:0.5-2.0

67. Addition of Micronutrients to Wastewater from Brewery

As Example 48, where the micronutrients are added as a dry powder with the use of a dry hopper and screw auger, or other means for delivering a dry powder.

68. Addition of Micronutrients to Wastewater from Brewery

As example 67, where the micronutrient powder is contains a weight percent of the individual micronutrients of from about 5.5% to about 28.6% (w/w) aluminum; from about 4.8% to about 9.1% (w/w) boron; from about 1.8% to 9.3% (w/w) cobalt; from about 9.5% to about 72.7% (w/w) magnesium; from about 7.3% to about 23.9% (w/w) manganese; and from about 3.6% to about 23.9% (w/w) zinc.

69. Addition of Micronutrients to Wastewater from Brewery

As Example 48, where the micronutrients are first mixed into citric acid, water, or other suitable solvent and delivered to the point of addition using pumps and pipes.

70. Dilution of Wastewater Streams

As example 48, where a portion of the treated effluent from the wastewater treatment is returned to the headworks of the plant to achieve a dilution of the influent wastewater.

71. Dilution of Wastewater Streams

As Example 70, where the treated effluent is returned to the headworks at a rate sufficient to equal ⅕ of the influent volume.

72. Dilution of Wastewater Streams

As Example 70, where the treated effluent is returned to the headworks at a rate sufficient to equal ¼ of the influent volume.

73. Dilution of Wastewater Streams

As Example 70, where the treated effluent is returned to the headworks at a rate sufficient to equal ⅓ of the influent volume.

74. Dilution of Wastewater Streams

As Example 70, where the treated effluent is returned to the headworks at a rate sufficient to equal ½ of the influent volume.

75. Dilution of Wastewater Streams

As Example 70, where the treated effluent is returned to the headworks at a rate sufficient to equal the influent volume.

76. Modulating pH of Wastewater Streams

As example 48, where the pH of the influent wastewater is adjusted up by adding calcium oxide, calcium hydroxide, sodium hydroxide, magnesium hydroxide, or other alkaline chemical.

77. Modulating pH of Wastewater Streams

As example 76, where the added chemical is food grade.

78. Modulating pH of Wastewater Streams

As Example 48, where the pH of the influent wastewater is adjusted down using hydrochloric acid, nitric acid, or other acidic chemical.

79. Modulating pH of Wastewater Streams

As Example 78, where the added chemical is food grade.

80. Size of Aerobic Basins

As Example 48, where the hydraulic retention time of the aerobic basins is modified by building additional basins, by building dividers within the existing a-basins, or by building other structures that increase or decrease the size of the aerobic basins.

81. Hydraulic Residence Time

As Example 48, where the hydraulic residence time equals that specified in Metcalf and Eddy Inc. 1991. *Wastewater Engineering: Treatment, Disposal, and Reuse*. Tchobanoglous, G. and Burton F. (eds). Irwin McGraw-Hill: New York; Montréal for a "complete mix" or "high-rate aeration" system.

82. Measurement of Nitrogen and Phosphorus in Effluent

As Example 48, where the nitrate nitrogen, ammonia nitrogen, and total phosphorus are measured in the effluent.

83. Control of Nitrogen and Phosphorus Levels

As Example 82, where the rate of addition of nitrogen to the system is reduced if the effluent nitrogen exceeds the permitted level.

84. Control of Nitrogen and Phosphorus Levels

As Example 82, where the rate of addition of nitrogen to the system is reduced if an increase in nitrate is observed in the effluent.

85. Control of Nitrogen and Phosphorus Levels

As Example 82, where the rate of addition of nitrogen to the system is reduced if an increase in ammonia is observed in the effluent.

86. Control of Nitrogen and Phosphorus Levels

As Example 82, where the rate of addition of nitrogen to the system is increased if a residual of nitrate of ammonia is not measured in the effluent.

87. Determination of Micronutrient Levels

As Example 48, where the micronutrient addition is determined from successful results from the laboratory scale experimentation.

88. Modulation of Microbial Species or Constituent Thereof.

As Example 48, where a plurality of conditions is examined to determine where the modulation of a particular microbial species or cellular constituent occurs.

89. Measurement of SSV

As Example 48, where the SSV and filamentous bacteria concentration are determined prior to the addition of nitrogen, phosphorus, and micronutrients. The addition of these nutrients then begins and a time of one to three MCRTS is allowed to elapse. During this time, the SSV and filamentous bacteria are measured. If an increase in either SSV or filamentous bacteria concentration is observed, the micronutrient combination and concentration is altered using Tables A-F as a guide. If a decrease in either the SSV or filamentous bacteria concentration is observed, a reduction in MCRT is initiated. Simultaneously, modulations in microbial species and/or cellular constituents are monitored. This reduction continues until the desired modulation occurs and before an increase in SSV and/or filamentous bacteria concentration is measured.

90. Measurement of SSV

As Example 89, where the reduction of MCRT commences as soon as the addition of nitrogen, phosphorus, and micronutrients is initiated.

91. Measurement of SSV

As Example 89, where the reduction of MCRT continues until an increase in SSV occurs. After the increase in SSV is observed, the MCRT is increased to the value evaluated prior to the increase in SSV. Thus, if the increase in SSV is observed at 6 days, the MCRT is increased to 6.5 or 7 days.

92. Measurement of Micronutrients

As Example 48, where the micronutrients in the wastewater are measured using methods of flame atomic absorption spectrometry and graphite furnace (or electrothermal) atomic absorption spectrometry (GFAAS or ETAAS), Laser-Induced Breakdown Spectroscopy (LIBS), inductively coupled plasma optical emission spectrometry (ICP-OES, ICP-AES), inductively coupled plasma mass spectrometry (ICP-MS), and/or spectrophotometry methods.

93. Origin of Wastewater

As Example 48, where the wastewater treatment plant is dedicated to a distillery, a palm oil mill, a fruit juice production facility and the like, a potato processor, a wet corn or rice mill, a sugar manufacturer, a citrate producer, a yeast manufacturer, a meat rendering processes and other food production processes that release food-grade biological oxygen demand into effluent water.

94. Production of Animal Feed Using Wastewater from Food Producing Facility Comprising an Aerobic Wastewater Treatment Plant As Example 48, where a full-scale producer of food products with a dedicated aerobic, biological wastewater treatment plant is located. Metals concentrations from the effluent from the brewery are determined using inductively coupled plasma spectroscopy (ICP). The historical biological oxygen demand in the wastewater is determined from plant records, if possible. Otherwise, BOD levels are determined using the Standard Method (Standard Methods for the Examination of Water and Wastewater, $22^{nd}$ edition, E. U. Rice et. al, editors. 2012. *American Public Health Association, American Water Works Association, Water Environment Federation*, publishers. Washington, D.C. USA). Plumbing is installed so that a portion of the treated influent from the wastewater treatment plant is returned to the head works so that the influent wastewater is diluted with the treated effluent. A chemical delivery system is constructed so that nitrogen, phosphorus, and micronutrients are added to the influent wastewater stream to achieve a BOD:N:P ratio of about 100:10:1 and concentrations of micronutrients as shown in Tables A-F in the aerobic basin. The aerobic basin volume is modified to achieve the hydraulic retention times specified for a complete mix system as specified in Metcalf and Eddy Inc. 1991. *Wastewater Engineering: Treatment, Disposal, and Reuse*. Tchobanoglous, G. and Burton F. (eds). Irwin McGraw-Hill: New York; Montréal. Dissolved oxygen levels in the aerobic basin are maintained at 1.5-2.5 mg/L by adjusting the rate of flow from the blowers, compressors, or other type of air delivery devices present at the wastewater treatment facility. The mean cell residence time (MCRT) is controlled by wasting cells from the wastewater treatment plant to achieve the lowest MCRT where the settling characteristics allow for the meeting of permitted or targeted total suspended solids levels in the effluent. The resulting biosolid mass is then used as an animal feed ingredient.

95. Addition of Aerobic Basin Volume

As Example 94, where the aerobic basin volume is increased by adding additional aerobic basin volume.

96. Reduction of Aerobic Basin Volume

As Example 94, where the aerobic basin volume is decreased by ceasing to use one or more existing aerobic basins or by hydraulically dividing an existing aerobic basin by adding a wall or other type of barrier that prohibits the use of part of the volume of the aerobic basin.

97. Reduction of Aerobic Basin Volume

As Example 96, where the aerobic basin volume is decreased by adding inert material to the existing basin such as sand, rocks, or soil.

98. Reduction of Aerobic Basin Volume

As Example 96, where this inert material is covered with a rubber liner or similar material to isolate the inert material from the aerobic wastewater volume.

99. Biomass as Animal Feed

As in Example 39, where the wasted biomass (WAS) is collected, stabilized by drying to a moisture content of approximately 12% or less, and included in feeds for animals.

100. Biomass as Animal Feed

As in Example 39, where the wasted biomass (WAS) is collected, stabilized by drying to a moisture content of approximately 12% or less, and fed to animals.

TABLE A

Aluminum Micronutrient Combinations

| ALUMINUM (60 mg/day/lb BOD/day-285 mg/day/lb BOD/day) | B | Co | Mg | Mn | Zn |
|---|---|---|---|---|---|
| Aluminum Alone | | | | | |
| All units are mg/day/lb BOD/day | x | x | x | x | x |
| Aluminum + 1 Micronutrient | | | | | |
| | 115-300 | 50-500 | ≥100 | 65-220 | 115-275 |
| Aluminum + 2 Micronutrients | | | | | |
| B (115-300 mg/day/lb BOD/day) | x | 50-500 | ≥100 | 65-220 | 115-275 |
| Co (50-500 mg/day/lb BOD/day) | x | x | ≥100 | 65-220 | 115-275 |
| Mg (>100 mg/day/lb BOD/day) | x | x | x | 65-220 | 115-275 |
| Mn (65-220 mg/day/lb BOD/day) | x | x | x | x | 115-275 |
| Aluminum + 3 Micronutrients | | | | | |
| B (115-300 mg/day/lb BOD/day) + Co (0.01-3.9 ppm) | x | x | ≥100 | 65-220 | 115-275 |
| B (115-300 mg/day/lb BOD/day) + Mg >100 mg/day/lb BOD/day) | x | x | x | 65-220 | 115-275 |
| B (115-300 mg/day/lb BOD/day) + Mn (0.04-1.0 ppm) | x | x | x | x | 115-275 |
| Co (50-500 mg/day/lb BOD/day) + Mg (>100 mg/day/lb BOD/day) | x | x | x | 65-220 | 115-275 |
| Mg (>100 mg/day/lb BOD/day) + Mn (65-220 mg/day/lb BOD/day) | x | x | x | x | 115-275 |
| Aluminum + 4 Micronutrients | | | | | |
| B (115-300 mg/day/lb BOD/day) + Co (50-500 mg/day/lb BOD/day) + Mg (>100 mg/day/lb BOD/day) | x | x | x | 65-220 | 115-275 |
| B (115-300 mg/day/lb BOD/day) + Co (50-500 mg/day/lb BOD/day) + Mn (65-220 mg/day/lb BOD/day) | x | x | x | x | 115-275 |
| B (115-300 mg/day/lb BOD/day) + Mg (>100 mg/day/lb BOD/day) + Mn (65-220 mg/day/lb BOD/day) | x | x | x | x | 115-275 |
| Co (50-500 mg/day/lb BOD/day) + Mg (>100 mg/day/lb BOD/day) + Mn (65-220 mg/day/lb BOD/day) | x | x | x | x | 115-275 |
| Aluminum + 5 Micronutrients | | | | | |
| B (115-300 mg/day/lb BOD/day) + Co (50-500 mg/day/lb BOD/day) + Mg (>100 mg/day/lb BOD/day) + Zn (115-275 mg/day/lb BOD/day) | x | x | x | x | x |

TABLE B

Boron Micronutrient Combinations

| BORON (115 mg/day/lb BOD/day-300 mg/day/lb BOD/day) | Al | Co | Mg | Mn | Zn |
|---|---|---|---|---|---|
| Boron Alone | | | | | |
| All units are mg/day/lb BOD/day | x | x | x | x | x |
| Boron + 1 Micronutrient | | | | | |
| | 60-285 | 50-500 | ≥100 | 65-220 | 115-275 |
| Boron + 2 Micronutrients | | | | | |
| Al (60-285 mg/day/lb BOD/day) | X | 50-500 | ≥100 | 65-220 | 115-275 |
| Co (50-500 mg/day/lb BOD/day) | x | x | ≥100 | 65-220 | 115-275 |
| Mg (≥100 mg/day/lb BOD/day) | x | x | x | 65-220 | 115-275 |
| Mn (65-220 mg/day/lb BOD/day) | x | x | x | x | 115-275 |
| Boron + 3 Micronutrients | | | | | |
| Al (60-285 mg/day/lb BOD/day) + Co (50-500 mg/day/lb BOD/day) | x | x | ≥100 | 65-220 | 115-275 |
| Al (60-285 mg/day/lb BOD/day) + Mg (≥100 mg/day/lb BOD/day) | x | x | x | 65-220 | 115-275 |
| Al (60-285 mg/day/lb BOD/day) + Mn (65-220 mg/day/lb BOD/day) | x | x | x | x | 115-275 |
| Co (50-500 mg/day/lb BOD/day) + Mg (≥100 mg/day/lb BOD/day) | x | x | x | 65-220 | 115-275 |
| Mg (≥100 mg/day/lb BOD/day) + Mn (65-220 mg/day/lb BOD/day) | x | x | x | x | 115-275 |

TABLE B-continued

Boron Micronutrient Combinations

| BORON (115 mg/day/lb BOD/day-300 mg/day/lb BOD/day) | Al | Co | Mg | Mn | Zn |
|---|---|---|---|---|---|
| Boron + 4 Micronutrients ||||||
| Al (60-285 mg/day/lb BOD/day) + Co (50-500 mg/day/lb BOD/day) + Mg (≥100 mg/day/lb BOD/day) | x | x | x | 65-220 | 115-275 |
| Al (60-285 mg/day/lb BOD/day) + Co (50-500 mg/day/lb BOD/day) + Mn (65-220 mg/day/lb BOD/day) | x | x | x | x | 115-275 |
| Al (60-285 mg/day/lb BOD/day) + Mg (≥1100 mg/day/lb BOD/day) + Mn (65-220 mg/day/lb BOD/day) | x | x | x | x | 115-275 |
| Co (50-500 mg/day/lb BOD/day) + Mg (≥1100 mg/day/lb BOD/day) + Mn (65-220 mg/day/lb BOD/day) | x | x | x | x | 115-275 |
| Boron + 5 Micronutrients ||||||
| Al (60-285 mg/day/lb BOD/day) + Co (50-500 mg/day/lb BOD/day) + Mg (≥100 mg/day/lb BOD/day) + Zn (115-275 mg/day/lb BOD/day) | x | x | x | x | x |

TABLE C

Cobalt Micronutrient Combinations

| COBALT (50 mg/day/lb BOD/day-500 mg/day/lb BOD/day) | B | Al | Mg | Mn | Zn |
|---|---|---|---|---|---|
| Cobalt Alone ||||||
| All units are mg/day/lb BOD/day | x | x | x | x | x |
| Cobalt + 1 Micronutrient ||||||
|  | 115-300 | 60-285 | ≥100 | 65-220 | 115-275 |
| Cobalt + 2 Micronutrients ||||||
| B (115-300 mg/day/lb BOD/day) | x | 60-285 | ≥100 | 65-220 | 115-275 |
| Al (60-285 mg/day/lb BOD/day) | x | x | ≥100 | 65-220 | 115-275 |
| Mg (≥100 mg/day/lb BOD/day) | x | x | x | 65-220 | 115-275 |
| Mn (65-220 mg/day/lb BOD/day) | x | x | x | x | 115-275 |
| Cobalt + 3 Micronutrients ||||||
| B (115-300 mg/day/lb BOD/day) + Al (60-285 mg/day/lb BOD/day) | x | x | ≥100 | 65-220 | 115-275 |
| B (115-300 mg/day/lb BOD/day) + Mg (≥100 mg/day/lb BOD/day) | x | x | x | 65-220 | 115-275 |
| B (115-300 mg/day/lb BOD/day) + Mn (65-220 mg/day/lb BOD/day) | x | x | x | x | 115-275 |
| Al (60-285 mg/day/lb BOD/day) + Mg (≥100 mg/day/lb BOD/day) | x | x | x | 65-220 | 115-275 |
| Mg (≥100 mg/day/lb BOD/day) + Mn (65-220 mg/day/lb BOD/day) | x | x | x | x | 115-275 |
| Cobalt + 4 Micronutrients ||||||
| B (115-300 mg/day/lb BOD/day) + Al (60-285 mg/day/lb BOD/day) + Mg (≥100 mg/day/lb BOD/day) | x | x | x | 65-220 | 115-275 |
| B (115-300 mg/day/lb BOD/day) + Al (60-285 mg/day/lb BOD/day) + Mn (65-220 mg/day/lb BOD/day) | x | x | x | x | 115-275 |
| B (115-300 mg/day/lb BOD/day) + Mg (≥100 mg/day/lb BOD/day) + Mn (65-220 mg/day/lb BOD/day) | x | x | x | x | 115-275 |
| Al (60-285 mg/day/lb BOD/day) + Mg (≥100 mg/day/lb BOD/day) + Mn (65-220 mg/day/lb BOD/day) | x | x | x | x | 115-275 |
| Cobalt + 5 Micronutrients ||||||
| B (115-300 mg/day/lb BOD/day) + Al (60-285 mg/day/lb BOD/day) + Mg (≥100 mg/day/lb BOD/day) + Zn (115-275 mg/day/lb BOD/day) | x | x | x | x | x |

TABLE D

Magnesium Micronutrient Combinations

| MAGNESIUM (≥100 mg/day/lb BOD/day) | B | Co | Al | Mn | Zn |
|---|---|---|---|---|---|
| Magnesium Alone ||||||
| All units are mg/day/lb BOD/day | x | x | x | x | x |
| Magnesium + 1 Micronutrient ||||||
|  | 115-300 | 50-500 | 60-285 | 65-220 | 115-275 |
| Magnesium + 2 Micronutrients ||||||
| B (115-300 mg/day/lb BOD/day) | x | 50-500 | 60-285 | 65-220 | 115-275 |
| Co (50-500 mg/day/lb BOD/day) | x | x | 60-285 | 65-220 | 115-275 |

TABLE D-continued

Magnesium Micronutrient Combinations

| MAGNESIUM (≥100 mg/day/lb BOD/day) | B | Co | Al | Mn | Zn |
|---|---|---|---|---|---|
| Al (60-285 mg/day/lb BOD/day) | x | x | x | 65-220 | 115-275 |
| Mn (65-220 mg/day/lb BOD/day) | x | x | x | x | 115-275 |
| Magnesium + 3 Micronutrients | | | | | |
| B (115-300 mg/day/lb BOD/day) + Co (50-500 mg/day/lb BOD/day) | x | x | 60-285 | 65-220 | 115-275 |
| B (115-300 mg/day/lb BOD/day) + Al (60-285 mg/day/lb BOD/day) | x | x | x | 65-220 | 115-275 |
| B (115-300 mg/day/lb BOD/day) + Mn (65-220 mg/day/lb BOD/day) | x | x | x | x | 115-275 |
| Co (50-500 mg/day/lb BOD/day) + Al (60-285 mg/day/lb BOD/day) | x | x | x | 65-220 | 115-275 |
| Al (60-285 mg/day/lb BOD/day) + Mn (65-220 mg/day/lb BOD/day) | x | x | x | x | 115-275 |
| Magnesium + 4 Micronutrients | | | | | |
| B (115-300 mg/day/lb BOD/day) + Co (50-500 mg/day/lb BOD/day) + Mg (≥100 mg/day/lb BOD/day) | x | x | x | 65-220 | 115-275 |
| B (115-300 mg/day/lb BOD/day) + Co (50-500 mg/day/lb BOD/day) + Mn (65-220 mg/day/lb BOD/day) | x | x | x | x | 115-275 |
| B (115-300 mg/day/lb BOD/day) + Al (60-285 mg/day/lb BOD/day) + Mn (65-220 mg/day/lb BOD/day) | x | x | x | x | 115-275 |
| Co (50-500 mg/day/lb BOD/day) + Al (60-285 mg/day/lb BOD/day) + Mn (65-220 mg/day/lb BOD/day) | x | x | x | x | 115-275 |
| Magnesium + 5 Micronutrients | | | | | |
| B (115-300 mg/day/lb BOD/day) + Co (50-500 mg/day/lb BOD/day) + Al (60-285 mg/day/lb BOD/day) + Zn (115-275 mg/day/lb BOD/day) | x | x | x | x | x |

TABLE E

Manganese Micronutrient Combinations

| MANGANESE (65 mg/day/lb BOD/day-220 mg/day/lb BCD/day) | B | Co | Mg | Al | Zn |
|---|---|---|---|---|---|
| Manganese Alone | | | | | |
| All units are mg/day/lb BOD/day | x | x | x | x | x |
| Mangenese + 1 Micronutrient | | | | | |
|  | 115-300 | 50-500 | ≥100 | 60-285 | 115-275 |
| Manganese + 2 Micronutrients | | | | | |
| B (115-300 mg/day/lb BOD/day) | x | 50-500 | ≥100 | 60-285 | 115-275 |
| Co (50-500 mg/day/lb BOD/day) | x | x | ≥100 | 60-285 | 115-275 |
| Mg (≥100 mg/day/lb BOD/day) | x | x | x | 60-285 | 115-275 |
| Al (60-285 mg/day/lb BOD/day) | x | x | x | x | 115-275 |
| Manganese +3 Micronutrients | | | | | |
| B (115-300 mg/day/lb BOD/day) + Co (50-500 mg/day/lb BOD/day) | x | x | ≥100 | 60-285 | 115-275 |
| B (115-300 mg/day/lb BOD/day) + Mg (≥100 mg/day/lb BOD/day) | x | x | x | 60-285 | 115-275 |
| B (115-300 mg/day/lb BOD/day) + Al (60-285 mg/day/lb BOD/day) | x | x | x | x | 115-275 |
| Co (50-500 mg/day/lb BOD/day) + Mg (≥100 mg/day/lb BOD/day) | x | x | x | 60-285 | 115-275 |
| Mg (≥100 mg/day/lb BOD/day) + Al (60-285 mg/day/lb BOD/day) | x | x | x | x | 115-275 |
| Manganese + 4 Micronutrients | | | | | |
| B (115-300 mg/day/lb BOD/day) + Co (0.01-3.9 ppm) + Mg (≥100 mg/day/lb BOD/day) | x | x | x | 60-285 | 115-275 |
| B (115-300 mg/day/lb BOD/day) + Co (0.01-3.9 ppm) + Al (60-285 mg/day/lb BOD/day) | x | x | x | x | 115-275 |
| B (115-300 mg/day/lb BOD/day) + Mg (≥100 mg/day/lb BOD/day) + Al (60-285 mg/day/lb BOD/day) | x | x | x | x | 115-275 |
| Co (50-500 mg/day/lb BOD/day) + Mg (≥100 mg/day/lb BOD/day) + Al (60-285 mg/day/lb BOD/day) | x | x | x | x | 115-275 |
| Manganese + 5 Micronutrients | | | | | |
| B (115-300 mg/day/lb BOD/day) + Co (50-500 mg/day/lb BOD/day) + Mg (≥100 mg/day/lb BOD/day) + Zn (115-275 mg/day/lb BOD/day) | x | x | x | x | x |

TABLE F

| Zinc Micronutrient Combinations | | | | | |
|---|---|---|---|---|---|
| ZINC (115 mg/day/lb BOD/day-275 mg/day/lb BOD/day) | B | Co | Mg | Mn | Al |
| *Zinc Alone* | | | | | |
| All units are mg/day/lb BOD/day | x | x | x | x | x |
| *Zinc + 1 Micronutrient* | | | | | |
| | 115-300 | 50-500 | ≥100 | 65-220 | 60-285 |
| *Zinc + 2 Micronutrients* | | | | | |
| B (115-300 mg/day/lb BOD/day) | x | 50-500 | ≥100 | 65-220 | 60-285 |
| Co (50-500 mg/day/lb BOD/day) | x | x | ≥100 | 65-220 | 60-285 |
| Mg (≥100 mg/day/lb BOD/day) | x | x | x | 65-220 | 60-285 |
| Mn (65-220 mg/day/lb BOD/day) | x | x | x | x | 60-285 |
| *Zinc + 3 Micronutrients* | | | | | |
| B (115-300 mg/day/lb BOD/day) + Co (50-500 mg/day/lb BOD/day) | x | x | ≥100 | 65-220 | 60-285 |
| B (115-300 mg/day/lb BOD/day) + Mg (≥100 mg/day/lb BOD/day) | x | x | x | 65-220 | 60-285 |
| B (115-300 mg/day/lb BOD/day) + Mn (65-220 mg/day/lb BOD/day) | x | x | x | x | 60-285 |
| Co (50-500 mg/day/lb BOD/day) + Mg (≥100 mg/day/lb BOD/day) | x | x | x | 65-220 | 60-285 |
| Mg (≥100 mg/day/lb BOD/day) + Mn (65-220 mg/day/lb BOD/day) | x | x | x | x | 60-285 |
| *Zinc + 4 Micronutrients* | | | | | |
| B (115-300 mg/day/lb BOD/day) + Co (50-500 mg/day/lb BOD/day) + Mg (≥100 mg/day/lb BOD/day) | x | x | x | 65-220 | 60-285 |
| B (115-300 mg/day/lb BOD/day) + Co (50-500 mg/day/lb BOD/day) + Mn (65-220 mg/day/lb BOD/day) | x | x | x | x | 60-285 |
| B (115-300 mg/day/lb BOD/day) + Mg (≥100 mg/day/lb BOD/day) + Mn (65-220 mg/day/lb BOD/day) | x | x | x | x | 60-285 |
| Co (50-500 mg/day/lb BOD/day) + Mg (≥100 mg/day/lb BOD/day) + Mn (65-220 mg/day/lb BOD/day) | x | x | x | x | 60-285 |
| *Zinc + 5 Micronutrients* | | | | | |
| B(115-300 mg/day/lb BOD/day) + Co (50-500 mg/day/lb BOD/day) + Mg (≥100 mg/day/lb BOD/day) + Al (60-285 mg/day/lb BOD/day) | x | x | x | x | x |

We claim:

1. A method for growing microbial biomass comprising:
    (a) providing a wastewater stream;
    (b) determining the concentration of micronutrients selected from the group consisting of aluminum, boron, cobalt, magnesium, manganese, and zinc, and any combination thereof, in the wastewater stream;
    (c) determining the biological oxygen demand (BOD) normalized dose of the micronutrients;
    (d) modulating the concentration of at least one micronutrient in the wastewater stream to provide a micronutrient-modulated wastewater stream, whereby said micronutrient-modulated wastewater stream has (i) a BOD normalized dose of aluminum between about 60 mg/day/lb BOD/day and about 285 mg/day/lb BOD/day; (ii) a BOD normalized dose of boron between about 115 mg/day/lb BOD/day and about 300 mg/day/lb BOD/day; (iii) a BOD normalized dose of cobalt between about 50 mg/day/lb BOD/day and about 500 mg/day/lb BOD/day; (iv) a BOD normalized dose of magnesium of at least about 100 mg/day/lb BOD/day; (v) a BOD normalized dose of manganese between about 65 mg/day/lb BOD/day and about 220 mg/day/lb BOD/day; and (vi) a BOD normalized dose of zinc between about 115 mg/day/lb BOD/day and about 275 mg/day/lb BOD/day; and
    (e) growing microbial biomass in the micronutrient-modulated wastewater stream.

2. The method according to claim 1, further comprising determining the concentration of nitrogen and phosphorus and BOD in step (b), wherein the concentration of nitrogen, phosphorus and the BOD is modulated in step (d) to provide: (i) a BOD:nitrogen ratio of at least 100 mg/liter BOD:6-20 mg/liter nitrogen; and (ii) a BOD:phosphorus ratio of at least 100 mg/liter BOD:0.5-2 mg/liter phosphorus.

3. The method according to claim 1, wherein the settled sludge volume after sixty minutes ($SSV_{60}$) exhibited by the micronutrient-modulated wastewater stream following the growing microbial biomass of step (e) is reduced when compared with the $SSV_{60}$ of the wastewater stream prior to the modulating of step (d).

4. The method according to claim 1, wherein the growing of step (e) is carried out for a period of about 1 or more mean cell residence times (MCRT), and wherein the modulated wastewater stream obtained after step (e) exhibits a settled sludge volume after sixty minutes ($SSV_{60}$) which is at least 10% less than the $SSV_{60}$ exhibited by the wastewater stream prior to the modulating of step (d).

5. The method according to claim 1, wherein said growing of step (e) is carried out for a period of about 3 or more mean cell residence times (MCRTs), and wherein the modulated wastewater stream obtained after step (e) exhibits a settled sludge volume after sixty minutes ($SSV_{60}$) which is at least 10% less than the $SSV_{60}$ exhibited by the wastewater stream prior to the modulating of step (d).

6. The method according to claim 1, wherein said growing of step (e) is carried out for a period of about 3 or more mean cell residence times (MCRTs), and wherein the modulated wastewater stream obtained after step (e) exhibits a settled sludge volume after sixty minutes ($SSV_{60}$) which is at least 20% less than the $SSV_{60}$ exhibited by the wastewater stream prior to the modulating of step (d).

7. The method according to claim 5, wherein the modulated wastewater exhibits an $SSV_{60}$ which is at least 30% less than the $SSV_{60}$ exhibited by the wastewater stream prior to the modulating of step (d).

8. The method according to claim 1, wherein the modulating of step (d) comprises increasing the concentration of at least one micronutrient in the wastewater stream substrate.

9. The method according to claim 1, wherein the modulating of step (d) comprises decreasing the concentration of at least one micronutrient in the wastewater stream.

10. The method according to claim 9, wherein said decreasing the concentration comprises ion-exchange or precipitation of the at least one micronutrient.

11. The method according to claim 9, wherein said decreasing the concentration comprises decreasing, during or prior to the providing of step (a), the concentration of the at least one micronutrient in a production process generating the wastewater stream.

12. The method according to claim 1, wherein the modulated wastewater stream comprises (i) at least about 50% (w/w) protein; (ii) at least about 6.5% (w/w) crude fat; (iii) at least about 4% (w/w) of 60% saturated fatty acids; and (iv) at least about 0.004% (w/w) Coenzyme Q10.

13. The method according to claim 1, further comprising mixing a growth factor in the wastewater stream.

14. The method according to claim 13, wherein the growth factor is selected from the group consisting of yeast extracts, molasses, brewery wort press water, palm oil mill effluent, and waste products.

15. The method according to claim 13, wherein the growth factor is added following the modulating of step (d).

16. The method according to claim 1, wherein the providing of step (a) includes obtaining the wastewater stream from a food processing plant.

17. A method for growing microbial mass comprising:
(a) providing a wastewater stream;
(b) determining the concentration of a plurality of micronutrients in the wastewater stream, the micronutrients including aluminum, boron, calcium, cobalt, magnesium, manganese, and zinc, and determining the concentration of the macronutrients nitrogen and phosphorus in the wastewater stream;
(c) determining the biological oxygen demand (BOD) normalized dose of one or more of the micronutrients in the wastewater stream;
(d) modulating the concentration of at least one of the one or more micronutrients in the wastewater stream to provide a micronutrient-modulated wastewater stream, whereby said micronutrient-modulated wastewater stream has (i) a BOD normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt varies of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day;
(e) modulating the concentration of at least one macronutrient in the wastewater stream to provide a macronutrient-modulated wastewater stream that has (i) a BOD:nitrogen ratio of at least about 100 mg/liter BOD:6-20 mg/liter nitrogen; and (ii) a BOD:phosphorus ratio of at least about 100 mg/liter BOD:0.5-2 mg/liter phosphorus; and
(f) growing microbial biomass in the macronutrient-modulated and micronutrient-modulated wastewater stream.

18. The method according to claim 17, wherein the modulating of step (e) includes adding phosphorus in the form of phosphoric acid.

19. The method according to claim 18, wherein the modulating of step (e) includes adding nitrogen in the form of one or more of urea, ammonium nitrate, anhydrous ammonium and animal manure.

20. A micronutrient composition for growing bacterial mass comprising a mixture of micronutrients, the micronutrients comprising: aluminum; boron; calcium; cobalt; magnesium; manganese; and zinc, wherein the micronutrient composition is used to modulate the concentration of the micronutrients in an wastewater stream, wherein adding the micronutrient composition to the wastewater stream, the micronutrient-modulated wastewater stream has (i) a biological oxygen demand (BOD) normalized dose of aluminum of between about 60 mg/day/lb BOD/day and about 285 mg/day/lb BOD/day; (ii) a BOD normalized dose of boron of between about 115 mg/day/lb BOD/day and about 300 mg/day/lb BOD/day; (iii) a BOD normalized dose of cobalt of between about 50 mg/day/lb BOD/day and about 500 mg/day/lb BOD/day; (iv) a BOD normalized dose of magnesium of at least about 100 mg/day/lb BOD/day; (v) a BOD normalized dose of manganese of between about 65 mg/day/lb BOD/day and about 220 mg/day/lb BOD/day; and (vi) a BOD normalized dose of zinc of between about 115 mg/day/lb BOD/day and about 275 mg/day/lb BOD/day.

* * * * *